(12) United States Patent
Wu et al.

(10) Patent No.: US 8,029,959 B2
(45) Date of Patent: Oct. 4, 2011

(54) CHARGE CONTROL AGENT AND TONER COMPRISING THE SAME

(75) Inventors: Lin Wu, Wuhan (CN); Zhilin Xia, Wuhan (CN); Shuangquan Zhu, Wuhan (CN)

(73) Assignee: Hubei Dinglong Chemical Co., Ltd., Wuhan (CN)

( * ) Notice: Subject to any disclaimer, the term of this patent is extended or adjusted under 35 U.S.C. 154(b) by 957 days.

(21) Appl. No.: 11/752,522

(22) Filed: May 23, 2007

(65) Prior Publication Data

US 2008/0227012 A1 Sep. 18, 2008

(30) Foreign Application Priority Data

Mar. 12, 2007 (CN) .......................... 2007 1 0051647

(51) Int. Cl.
*G03G 9/097* (2006.01)
(52) U.S. Cl. .................. 430/108.3; 430/108.4; 556/121; 556/140; 556/141; 556/27; 556/52
(58) Field of Classification Search ............... 430/108.3, 430/108.4; 556/121, 140, 144, 27, 52, 58
See application file for complete search history.

(56) References Cited

U.S. PATENT DOCUMENTS

| | | | | |
|---|---|---|---|---|
| 5,188,929 | A | * | 2/1993 | Ishii .......................... 430/108.3 |
| 5,332,636 | A | * | 7/1994 | Ong .......................... 430/108.24 |
| 5,409,794 | A | * | 4/1995 | Ong .......................... 430/108.3 |
| 5,571,654 | A | * | 11/1996 | Ong .......................... 430/108.3 |
| 2001/0049068 | A1 | * | 12/2001 | Iemura et al. ............... 430/108.3 |
| 2003/0175607 | A1 | * | 9/2003 | Isoda et al. .................. 430/108.3 |
| 2006/0063082 | A1 | * | 3/2006 | Mikuriya et al. ........... 430/108.3 |
| 2006/0172210 | A1 | * | 8/2006 | Yamate et al. .............. 430/108.3 |

FOREIGN PATENT DOCUMENTS

JP 62218478 A * 9/1987

OTHER PUBLICATIONS

English language translation of JP 62-218478 (Sep. 1987).*
"Report of the American Schistosomiasis Delegation to the People's Republic of China", The American Journal of Tropical Medicine and Hygiene, vol. 26, No. 3, pp. 427-457 (1977).*

Ying, Hui-Qing. "Studies of the Chemical Structure of Sodium Antimony Gallate", Acta Chimica Sinica, vol. 39, No. 3, pp. 209-213 (Jun. 1981).*

* cited by examiner

*Primary Examiner* — Christopher Rodee
(74) *Attorney, Agent, or Firm* — Matthias Scholl P.C.; Matthias Scholl

(57) ABSTRACT

Taught herein is a charge control agent comprising a specific type of gallic acid metal complex represented by the following Chemical Formula (1) or Chemical Formula (2):

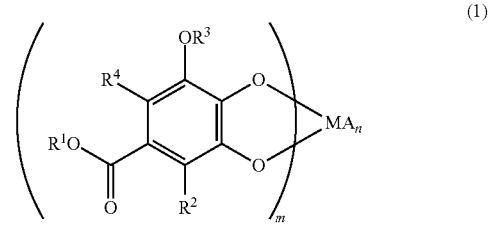

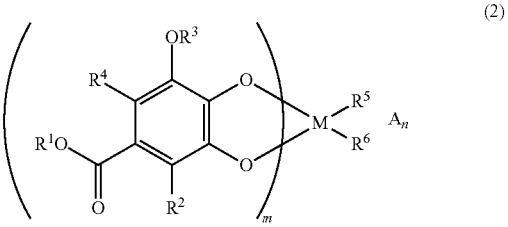

In the formula (1), $R^1$ represents an alkyl group containing 1-12 carbon atoms, an alkenyl group containing 1-12 carbon atoms, a substituted or unsubstituted aryl group containing 6-12 carbon atoms, or a hydrogen atom; $R^2$ and $R^4$ can independently represent an alkyl group containing 1-12 carbon atoms, an alkenyl group containing 2-12 carbon atoms, an alkoxy group containing 1-12 carbon atoms, a substituted or unsubstituted aryl group containing 6-12 carbon atoms, a halogen atom, or a hydrogen atom; $R^3$ represents an alkyl group containing 1-12 carbon atoms, a substituted or unsubstituted aryl group containing 6-12 carbon atoms, a potassium atom, a sodium atom or a hydrogen atom. M represents a divalent to tetravalent metal atom, A is a counterion, m is a number from 1 to 3, and n is 1 or 2.

2 Claims, 8 Drawing Sheets

Table 1

| Embodiment | Toner number | Charge control agent number | Charge amount (-μC/g) | | | | | | Charge stability (-μC/g) | |
|---|---|---|---|---|---|---|---|---|---|---|
| | | | 1 minute | 2 minute | 5 minute | 10 minute | 20 minute | 60 minute | Initial charge amount | Charge amount after storage |
| Embodiment 1 | 1 | 1-1 | 21.0 | 22.4 | 23.1 | 23.4 | 23.4 | 23.5 | 23.3 | 22.4 |
| Embodiment 2 | 2 | 1-2 | 21.1 | 22.2 | 22.5 | 22.6 | 22.7 | 22.8 | 22.6 | 22.1 |
| Embodiment 3 | 3 | 1-3 | 21.2 | 22.2 | 22.5 | 22.7 | 22.8 | 22.9 | 22.7 | 22.1 |
| Embodiment 4 | 4 | 1-4 | 21.3 | 22.6 | 22.9 | 23.1 | 23.1 | 23.4 | 23.1 | 22.5 |
| Embodiment 5 | 5 | 1-5 | 22.0 | 22.7 | 23.0 | 23.2 | 23.5 | 23.5 | 23.2 | 22.4 |
| Embodiment 6 | 6 | 1-6 | 22.1 | 23.0 | 23.1 | 23.1 | 23.1 | 23.1 | 23.0 | 21.9 |
| Embodiment 7 | 7 | 1-7 | 20.9 | 21.4 | 22.3 | 22.5 | 22.6 | 22.5 | 22.5 | 20.5 |
| Embodiment 8 | 8 | 1-8 | 20.9 | 21.3 | 21.6 | 21.9 | 22.1 | 22.1 | 21.9 | 20.0 |
| Embodiment 9 | 9 | 1-9 | 21.0 | 21.9 | 22.4 | 22.6 | 22.6 | 22.5 | 22.6 | 21.3 |
| Embodiment 10 | 10 | 1-10 | 20.8 | 21.2 | 21.6 | 21.9 | 22.0 | 22.1 | 21.8 | 21.0 |
| Embodiment 11 | 11 | 1-11 | 20.8 | 21.3 | 21.7 | 21.9 | 22.1 | 22.0 | 21.9 | 20.5 |
| Embodiment 12 | 12 | 1-12 | 20.9 | 22.0 | 22.4 | 22.6 | 22.7 | 22.7 | 22.6 | 20.9 |
| Embodiment 13 | 13 | 1-13 | 21.1 | 22.3 | 23.0 | 23.3 | 23.4 | 23.4 | 23.3 | 21.0 |
| Embodiment 14 | 14 | 1-14 | 20.8 | 21.9 | 22.3 | 22.2 | 22.3 | 22.2 | 22.2 | 20.1 |
| Embodiment 15 | 15 | 1-15 | 20.1 | 21.8 | 22.3 | 22.4 | 22.5 | 22.5 | 22.3 | 20.3 |
| Embodiment 16 | 16 | 1-16 | 20.1 | 22.0 | 22.4 | 22.3 | 22.3 | 22.3 | 22.3 | 20.0 |
| Embodiment 17 | 17 | 1-17 | 20.0 | 21.5 | 22.3 | 22.4 | 22.5 | 22.5 | 22.4 | 20.3 |
| Embodiment 18 | 18 | 1-18 | 20.0 | 21.3 | 21.5 | 21.6 | 21.5 | 21.6 | 21.6 | 20.0 |
| Embodiment 19 | 19 | 1-19 | 20.1 | 21.3 | 21.7 | 21.7 | 21.8 | 21.7 | 21.7 | 19.9 |
| Embodiment 20 | 20 | 1-20 | 20.0 | 21.3 | 21.4 | 21.5 | 21.7 | 21.8 | 21.5 | 19.4 |
| Embodiment 21 | 21 | 1-21 | 20.1 | 21.7 | 22.3 | 22.6 | 22.7 | 22.7 | 22.6 | 21.0 |
| Embodiment 22 | 22 | 1-22 | 21.5 | 22.6 | 23.5 | 23.7 | 23.7 | 23.7 | 23.5 | 21.1 |
| Embodiment 23 | 23 | 1-27 | 21.4 | 22.3 | 22.8 | 23.1 | 23.2 | 23.2 | 23.1 | 20.5 |
| Embodiment 24 | 24 | 1-30 | 20.6 | 21.3 | 21.6 | 21.9 | 22.0 | 22.0 | 21.9 | 20.1 |
| Embodiment 25 | 25 | 1-33 | 20.1 | 21.7 | 22.3 | 22.8 | 22.9 | 22.9 | 22.8 | 21.0 |
| Embodiment 26 | 26 | 1-37 | 20.6 | 21.9 | 22.5 | 22.8 | 23.0 | 23.0 | 22.6 | 21.2 |
| Embodiment 27 | 27 | 1-38 | 20.5 | 21.5 | 21.7 | 21.7 | 21.7 | 21.6 | 21.7 | 20.0 |
| Embodiment 28 | 28 | 2-1 | 21.4 | 22.5 | 23.8 | 23.9 | 23.9 | 23.8 | 23.9 | 22.1 |
| Embodiment 29 | 29 | 2-10 | 21.6 | 22.7 | 23.1 | 23.5 | 23.7 | 23.8 | 23.5 | 21.2 |
| Comparative Embodiment 1 | Comparative Embodiment 1 | E-81 | 21.7 | 25.8 | 29.1 | 30.3 | 32.6 | 29.8 | 30.3 | 17.5 |
| Comparative Embodiment 2 | Comparative Embodiment 2 | S-34 | 19.4 | 23.5 | 26.7 | 28.5 | 26.3 | 25.4 | 28.5 | 15.4 |
| Comparative Embodiment 3 | Comparative Embodiment 3 | E-88 | 12.3 | 14.3 | 15.4 | 16.0 | 16.4 | 16.0 | 16.0 | 14.3 |

FIG. 1

Table 2

| Embodiment | 20°C/50%RH | | | | | | | | 35°C/85%RH | | | | | | | |
|---|---|---|---|---|---|---|---|---|---|---|---|---|---|---|---|---|
| | Initial stage | | | | 500,000 | | | | Initial stage | | | | 500,000 | | | |
| | Image density | Fog | Resolution | Charge amount | Image density | Fog | Resolution | Charge amount | Image density | Fog | Resolution | Charge amount | Image density | Fog | Resolution | Charge amount |
| 1 | 1.41 | 0.001 | 7.0 | 23.3 | 1.42 | 0.001 | 6.0 | 21.2 | 1.42 | 0.001 | 7.0 | 21.3 | 1.43 | 0.001 | 7.0 | 21.0 |
| 2 | 1.41 | 0.001 | 7.0 | 22.6 | 1.42 | 0.002 | 6.0 | 20.1 | 1.42 | 0.001 | 7.0 | 20.6 | 1.42 | 0.001 | 7.0 | 21.0 |
| 3 | 1.41 | 0.001 | 7.0 | 22.7 | 1.42 | 0.001 | 6.0 | 21.2 | 1.42 | 0.001 | 7.0 | 20.7 | 1.42 | 0.001 | 7.0 | 20.2 |
| 4 | 1.41 | 0.001 | 7.0 | 23.1 | 1.42 | 0.001 | 6.0 | 21.8 | 1.42 | 0.001 | 7.0 | 21.1 | 1.42 | 0.001 | 7.0 | 21.0 |
| 5 | 1.42 | 0.001 | 7.0 | 23.2 | 1.43 | 0.002 | 6.0 | 21.1 | 1.42 | 0.001 | 7.0 | 21.2 | 1.43 | 0.001 | 7.0 | 21.0 |
| 6 | 1.41 | 0.001 | 7.0 | 23.0 | 1.42 | 0.002 | 6.0 | 20.9 | 1.42 | 0.001 | 7.0 | 22.0 | 1.42 | 0.001 | 7.0 | 21.4 |
| 7 | 1.41 | 0.001 | 7.0 | 22.5 | 1.42 | 0.001 | 6.0 | 20.1 | 1.42 | 0.001 | 7.0 | 21.4 | 1.42 | 0.001 | 7.0 | 21.0 |
| 8 | 1.41 | 0.001 | 7.0 | 21.9 | 1.42 | 0.001 | 6.0 | 20.1 | 1.42 | 0.001 | 7.0 | 20.0 | 1.42 | 0.001 | 7.0 | 19.3 |
| 9 | 1.42 | 0.001 | 7.0 | 22.6 | 1.42 | 0.001 | 6.0 | 20.5 | 1.42 | 0.001 | 7.0 | 20.6 | 1.42 | 0.001 | 7.0 | 19.9 |
| 10 | 1.41 | 0.001 | 7.0 | 21.8 | 1.41 | 0.002 | 6.0 | 19.9 | 1.42 | 0.001 | 7.0 | 21.9 | 1.43 | 0.001 | 7.0 | 21.1 |
| 11 | 1.41 | 0.001 | 7.0 | 21.9 | 1.42 | 0.002 | 6.0 | 19.8 | 1.42 | 0.001 | 7.0 | 20.3 | 1.42 | 0.001 | 7.0 | 20.0 |
| 12 | 1.41 | 0.001 | 7.0 | 22.6 | 1.42 | 0.001 | 6.0 | 20.4 | 1.42 | 0.001 | 7.0 | 20.4 | 1.42 | 0.001 | 7.0 | 20.2 |
| 13 | 1.41 | 0.001 | 7.0 | 23.3 | 1.42 | 0.001 | 6.0 | 21.2 | 1.42 | 0.001 | 7.0 | 20.3 | 1.42 | 0.001 | 7.0 | 20.1 |
| 14 | 1.42 | 0.001 | 7.0 | 22.2 | 1.41 | 0.001 | 6.0 | 21.0 | 1.42 | 0.001 | 7.0 | 20.1 | 1.42 | 0.001 | 7.0 | 19.8 |
| 15 | 1.41 | 0.001 | 7.0 | 22.3 | 1.42 | 0.002 | 6.0 | 20.3 | 1.42 | 0.001 | 7.0 | 20.3 | 1.42 | 0.001 | 7.0 | 19.4 |
| 16 | 1.41 | 0.001 | 7.0 | 22.3 | 1.42 | 0.001 | 6.0 | 20.2 | 1.42 | 0.001 | 7.0 | 20.4 | 1.42 | 0.001 | 7.0 | 19.5 |
| 17 | 1.41 | 0.001 | 7.0 | 22.4 | 1.42 | 0.001 | 6.0 | 21.0 | 1.42 | 0.001 | 7.0 | 20.1 | 1.42 | 0.001 | 7.0 | 19.3 |
| 18 | 1.41 | 0.001 | 7.0 | 21.6 | 1.42 | 0.001 | 6.0 | 20.0 | 1.42 | 0.001 | 7.0 | 20.0 | 1.42 | 0.001 | 7.0 | 19.2 |
| 19 | 1.41 | 0.001 | 7.0 | 21.7 | 1.42 | 0.001 | 6.0 | 20.1 | 1.42 | 0.001 | 7.0 | 19.9 | 1.42 | 0.002 | 7.0 | 19.0 |
| 20 | 1.41 | 0.001 | 7.0 | 21.5 | 1.42 | 0.002 | 6.0 | 19.7 | 1.42 | 0.001 | 7.0 | 19.8 | 1.42 | 0.002 | 7.0 | 18.4 |
| 21 | 1.41 | 0.001 | 7.0 | 22.6 | 1.41 | 0.001 | 6.0 | 21.0 | 1.42 | 0.001 | 7.0 | 21.0 | 1.42 | 0.001 | 7.0 | 19.3 |
| 22 | 1.41 | 0.001 | 7.0 | 23.5 | 1.42 | 0.001 | 6.0 | 21.2 | 1.42 | 0.001 | 7.0 | 21.3 | 1.43 | 0.001 | 7.0 | 19.2 |
| 23 | 1.42 | 0.001 | 7.0 | 23.1 | 1.42 | 0.001 | 6.0 | 21.3 | 1.42 | 0.001 | 7.0 | 21.4 | 1.42 | 0.001 | 7.0 | 19.5 |
| 24 | 1.41 | 0.001 | 7.0 | 21.9 | 1.42 | 0.001 | 6.0 | 20.1 | 1.42 | 0.001 | 7.0 | 20.0 | 1.43 | 0.002 | 7.0 | 18.9 |
| 25 | 1.41 | 0.001 | 7.0 | 22.8 | 1.42 | 0.001 | 6.0 | 20.3 | 1.42 | 0.001 | 7.0 | 21.0 | 1.42 | 0.001 | 7.0 | 20.1 |
| 26 | 1.41 | 0.001 | 7.0 | 22.6 | 1.41 | 0.002 | 6.0 | 20.3 | 1.42 | 0.001 | 7.0 | 21.0 | 1.42 | 0.001 | 7.0 | 20.3 |
| 27 | 1.41 | 0.001 | 7.0 | 21.7 | 1.42 | 0.002 | 6.0 | 19.9 | 1.42 | 0.001 | 7.0 | 19.8 | 1.42 | 0.001 | 7.0 | 19.0 |
| 28 | 1.41 | 0.001 | 7.0 | 23.9 | 1.42 | 0.001 | 6.0 | 21.0 | 1.42 | 0.001 | 7.0 | 21.4 | 1.42 | 0.001 | 7.0 | 20.3 |
| 29 | 1.41 | 0.001 | 7.0 | 23.5 | 1.42 | 0.001 | 6.0 | 21.3 | 1.42 | 0.001 | 7.0 | 21.3 | 1.42 | 0.001 | 7.0 | 20.0 |
| Comp.1 | 1.35 | 0.001 | 7.0 | 30.3 | 1.42 | 0.012 | 4.0 | 25.3 | 1.42 | 0.001 | 7.0 | 29.3 | 1.32 | 0.014 | 4.0 | 15.6 |
| Comp.2 | 1.37 | 0.001 | 7.0 | 28.5 | 1.43 | 0.011 | 4.0 | 20.1 | 1.42 | 0.001 | 7.0 | 27.4 | 1.31 | 0.013 | 4.0 | 14.6 |
| Comp.3 | 1.44 | 0.002 | 7.0 | 16.0 | 1.45 | 0.013 | 3.0 | 13.2 | 1.42 | 0.002 | 7.0 | 14.9 | 1.31 | 0.014 | 3.0 | 10.3 |

FIG. 2

Table 3

| Embodiment | Toner number | Charge control agent number | Charge amount (-μC/g) | | | | | | Charge stability (-μC/g) | |
|---|---|---|---|---|---|---|---|---|---|---|
| | | | 1 minute | Charge amount after storage | Charge amount after storage | 10 minute | 20 minute | 60 minute | Initial stage charge amount | Charge amount after storage |
| 30 | 30 | 1-1 | 21.1 | 22.3 | 23.0 | 23.2 | 23.3 | 23.4 | 23.2 | 22.1 |
| 31 | 31 | 1-2 | 21.0 | 22.0 | 22.2 | 22.4 | 22.5 | 22.6 | 22.4 | 20.9 |
| 32 | 32 | 1-3 | 21.1 | 22.3 | 22.4 | 22.4 | 22.5 | 22.6 | 22.4 | 20.7 |
| 33 | 33 | 1-4 | 21.3 | 22.5 | 22.7 | 23.0 | 23.1 | 23.3 | 21.9 | 21.8 |
| 34 | 34 | 1-5 | 21.9 | 22.6 | 23.1 | 23.3 | 23.6 | 23.7 | 23.3 | 21.8 |
| 35 | 35 | 1-6 | 22.2 | 23.1 | 23.3 | 23.5 | 23.4 | 23.2 | 23.5 | 21.5 |
| 36 | 36 | 1-7 | 20.7 | 21.3 | 22.2 | 22.4 | 22.5 | 22.5 | 22.5 | 20.7 |
| 37 | 37 | 1-8 | 20.8 | 21.2 | 21.5 | 21.6 | 22.0 | 22.0 | 21.7 | 20.0 |
| 38 | 38 | 1-9 | 21.0 | 21.7 | 22.6 | 22.7 | 22.8 | 22.8 | 22.8 | 21.1 |
| 39 | 39 | 1-10 | 20.7 | 21.1 | 21.5 | 21.7 | 22.1 | 22.2 | 21.7 | 20.1 |
| 40 | 40 | 1-11 | 20.7 | 21.3 | 21.6 | 21.8 | 22.3 | 22.2 | 21.8 | 20.1 |
| 41 | 41 | 1-12 | 20.4 | 21.9 | 22.2 | 22.4 | 22.5 | 22.7 | 22.4 | 21.0 |
| 42 | 42 | 1-13 | 21.0 | 22.3 | 23.1 | 23.5 | 23.6 | 23.6 | 23.5 | 21.8 |
| 43 | 43 | 1-14 | 20.7 | 21.8 | 22.0 | 22.2 | 22.3 | 22.4 | 22.3 | 21.0 |
| 44 | 44 | 1-15 | 20.3 | 21.9 | 22.4 | 22.5 | 22.6 | 22.7 | 22.5 | 21.2 |
| 45 | 45 | 1-16 | 20.0 | 21.9 | 22.3 | 22.4 | 22.4 | 22.5 | 22.4 | 21.1 |
| 46 | 46 | 1-17 | 20.0 | 21.4 | 22.2 | 22.4 | 22.6 | 22.7 | 22.4 | 21.1 |
| 47 | 47 | 1-18 | 20.0 | 21.2 | 21.4 | 21.5 | 21.6 | 21.7 | 21.5 | 20.0 |
| 48 | 48 | 1-19 | 20.1 | 21.6 | 21.8 | 21.9 | 22.0 | 22.1 | 21.8 | 19.9 |
| 49 | 49 | 1-20 | 20.2 | 21.6 | 21.8 | 22.1 | 22.1 | 22.2 | 22.1 | 20.1 |
| 50 | 50 | 1-21 | 20.4 | 21.9 | 22.4 | 22.8 | 22.9 | 22.9 | 22.8 | 20.3 |
| 51 | 51 | 1-22 | 21.6 | 22.7 | 23.8 | 23.7 | 23.8 | 23.9 | 23.7 | 21.4 |
| 52 | 52 | 1-27 | 21.4 | 22.5 | 22.9 | 23.3 | 23.5 | 23.5 | 23.5 | 21.5 |
| 53 | 53 | 1-30 | 20.7 | 21.6 | 21.6 | 21.7 | 21.7 | 21.7 | 21.7 | 20.4 |
| 54 | 54 | 1-33 | 20.2 | 21.6 | 22.6 | 22.6 | 22.7 | 22.7 | 22.6 | 21.0 |
| 55 | 55 | 1-37 | 20.6 | 22.0 | 22.7 | 22.9 | 23.0 | 23.3 | 22.9 | 21.1 |
| 56 | 56 | 1-38 | 20.7 | 21.6 | 29.0 | 22.0 | 22.1 | 22.4 | 22.1 | 20.0 |
| 57 | 57 | 2-1 | 21.9 | 23.0 | 23.9 | 24.0 | 24.0 | 23.8 | 24.0 | 22.1 |
| 58 | 58 | 2-10 | 21.9 | 23.0 | 23.5 | 23.6 | 23.8 | 23.8 | 23.6 | 21.4 |
| Comp.4 | Comp.4 | E-81 | 19.4 | 22.6 | 24.6 | 26.8 | 29.1 | 30.3 | 26.8 | 18.3 |
| Comp.5 | Comp.5 | S-34 | 14.6 | 19.0 | 21.3 | 23.6 | 27.4 | 28.1 | 23.6 | 16.5 |
| Comp.6 | Comp.6 | E-88 | 10.2 | 12.4 | 15.4 | 16.9 | 17.3 | 17.8 | 16.4 | 12.1 |

FIG. 3

Table 4

| Embodiment | 20°C/50%RH | | | | | | | | 35°C/85%RH | | | | | | | |
|---|---|---|---|---|---|---|---|---|---|---|---|---|---|---|---|---|
| | Initial stage | | | | 500,00 | | | | Initial stage | | | | 500,000 | | | |
| | Image density | Fog | Resolution | Charge amount | Image density | Fog | Resolution | Charge amount | Image density | Fog | Resolution | Charge amount | Image density | Fog | Resolution | Charge amount |
| 30 | 1.41 | 0.001 | 8.0 | 23.2 | 1.42 | 0.001 | 7.0 | 21.2 | 1.42 | 0.001 | 8.0 | 23.1 | 1.42 | 0.001 | 8.0 | 22.4 |
| 31 | 1.41 | 0.001 | 8.0 | 22.4 | 1.42 | 0.001 | 7.0 | 21.0 | 1.42 | 0.001 | 8.0 | 22.3 | 1.42 | 0.001 | 8.0 | 22.0 |
| 32 | 1.41 | 0.001 | 8.0 | 22.4 | 1.42 | 0.001 | 7.0 | 20.9 | 1.42 | 0.001 | 8.0 | 22.3 | 1.42 | 0.001 | 8.0 | 22.1 |
| 33 | 1.42 | 0.001 | 8.0 | 21.9 | 1.42 | 0.001 | 7.0 | 20.2 | 1.42 | 0.001 | 8.0 | 21.8 | 1.42 | 0.001 | 8.0 | 21.5 |
| 34 | 1.41 | 0.001 | 8.0 | 23.3 | 1.42 | 0.001 | 7.0 | 21.3 | 1.43 | 0.001 | 8.0 | 23.2 | 1.43 | 0.001 | 8.0 | 23.0 |
| 35 | 1.41 | 0.001 | 8.0 | 23.5 | 1.42 | 0.001 | 7.0 | 21.2 | 1.42 | 0.001 | 8.0 | 23.4 | 1.42 | 0.001 | 8.0 | 23.1 |
| 36 | 1.41 | 0.001 | 8.0 | 22.5 | 1.42 | 0.001 | 7.0 | 21.0 | 1.42 | 0.001 | 8.0 | 22.4 | 1.42 | 0.001 | 8.0 | 22.3 |
| 37 | 1.41 | 0.001 | 8.0 | 21.7 | 1.42 | 0.001 | 7.0 | 20.1 | 1.43 | 0.001 | 8.0 | 21.6 | 1.43 | 0.001 | 8.0 | 21.4 |
| 38 | 1.41 | 0.001 | 8.0 | 22.8 | 1.42 | 0.001 | 7.0 | 21.6 | 1.42 | 0.001 | 8.0 | 22.6 | 1.42 | 0.001 | 8.0 | 22.3 |
| 39 | 1.41 | 0.001 | 8.0 | 21.7 | 1.42 | 0.001 | 7.0 | 20.4 | 1.42 | 0.001 | 8.0 | 21.5 | 1.42 | 0.001 | 8.0 | 21.3 |
| 40 | 1.41 | 0.001 | 8.0 | 21.8 | 1.43 | 0.001 | 7.0 | 20.2 | 1.42 | 0.001 | 8.0 | 21.6 | 1.42 | 0.001 | 8.0 | 21.1 |
| 41 | 1.41 | 0.001 | 8.0 | 22.4 | 1.42 | 0.001 | 7.0 | 21.4 | 1.42 | 0.001 | 8.0 | 22.3 | 1.42 | 0.001 | 8.0 | 22.0 |
| 42 | 1.41 | 0.001 | 8.0 | 23.5 | 1.42 | 0.002 | 7.0 | 21.9 | 1.42 | 0.001 | 8.0 | 23.0 | 1.42 | 0.001 | 8.0 | 22. |
| 43 | 1.42 | 0.001 | 8.0 | 22.3 | 1.42 | 0.001 | 7.0 | 20.9 | 1.42 | 0.001 | 8.0 | 22.2 | 1.42 | 0.001 | 8.0 | 21.5 |
| 44 | 1.41 | 0.001 | 8.0 | 22.5 | 1.43 | 0.001 | 7.0 | 21.5 | 1.42 | 0.001 | 8.0 | 22.4 | 1.42 | 0.001 | 8.0 | 22.0 |
| 45 | 1.41 | 0.001 | 8.0 | 22.4 | 1.42 | 0.001 | 7.0 | 21.3 | 1.42 | 0.001 | 8.0 | 22.3 | 1.42 | 0.001 | 8.0 | 21.5 |
| 46 | 1.41 | 0.001 | 8.0 | 22.4 | 1.42 | 0.001 | 7.0 | 21.2 | 1.42 | 0.001 | 8.0 | 22.1 | 1.42 | 0.001 | 8.0 | 21.3 |
| 47 | 1.41 | 0.001 | 8.0 | 21.5 | 1.42 | 0.001 | 7.0 | 20.4 | 1.42 | 0.001 | 8.0 | 21.3 | 1.42 | 0.001 | 8.0 | 21.4 |
| 48 | 1.41 | 0.001 | 8.0 | 21.8 | 1.42 | 0.001 | 7.0 | 20.3 | 1.43 | 0.001 | 8.0 | 21.4 | 1.43 | 0.001 | 8.0 | 21.0 |
| 49 | 1.41 | 0.001 | 8.0 | 22.1 | 1.43 | 0.002 | 7.0 | 20.1 | 1.42 | 0.001 | 8.0 | 22.0 | 1.42 | 0.001 | 8.0 | 21.3 |
| 50 | 1.41 | 0.001 | 8.0 | 22.8 | 1.42 | 0.001 | 7.0 | 21.0 | 1.42 | 0.001 | 8.0 | 22.6 | 1.42 | 0.001 | 8.0 | 21.4 |
| 51 | 1.41 | 0.001 | 8.0 | 23.7 | 1.42 | 0.001 | 7.0 | 21.9 | 1.42 | 0.001 | 8.0 | 23.3 | 1.42 | 0.001 | 8.0 | 22.0 |
| 52 | 1.41 | 0.001 | 8.0 | 23.5 | 1.42 | 0.001 | 7.0 | 21.8 | 1.42 | 0.001 | 8.0 | 23.2 | 1.42 | 0.001 | 8.0 | 21.2 |
| 53 | 1.41 | 0.001 | 8.0 | 21.7 | 1.42 | 0.001 | 7.0 | 21.0 | 1.42 | 0.001 | 8.0 | 21.4 | 1.42 | 0.001 | 8.0 | 20.3 |
| 54 | 1.41 | 0.001 | 8.0 | 22.6 | 1.42 | 0.001 | 7.0 | 21.3 | 1.42 | 0.001 | 8.0 | 22.3 | 1.42 | 0.001 | 8.0 | 21.0 |
| 55 | 1.41 | 0.001 | 8.0 | 22.9 | 1.42 | 0.001 | 7.0 | 21.8 | 1.42 | 0.001 | 8.0 | 22.5 | 1.42 | 0.001 | 8.0 | 21.3 |
| 56 | 1.41 | 0.001 | 8.0 | 22.1 | 1.42 | 0.002 | 7.0 | 21.0 | 1.42 | 0.001 | 8.0 | 22.0 | 1.42 | 0.001 | 8.0 | 20.7 |
| 57 | 1.42 | 0.001 | 8.0 | 24.0 | 1.42 | 0.001 | 7.0 | 23.1 | 1.42 | 0.001 | 8.0 | 23.6 | 1.42 | 0.001 | 8.0 | 21.4 |
| 58 | 1.41 | 0.001 | 8.0 | 23.6 | 1.42 | 0.001 | 7.0 | 22.1 | 1.42 | 0.001 | 8.0 | 23.2 | 1.42 | 0.001 | 8.0 | 21.9 |
| Comp.4 | 1.41 | 0.001 | 8.0 | 26.8 | 1.41 | 0.012 | 4.0 | 23.0 | 1.42 | 0.001 | 8.0 | 24.5 | 1.34 | 0.012 | 4.0 | 13.2 |
| Comp.5 | 1.41 | 0.001 | 8.0 | 23.6 | 1.41 | 0.011 | 4.0 | 19.2 | 1.42 | 0.001 | 8.0 | 20.5 | 1.32 | 0.012 | 4.0 | 11.3 |
| Comp.6 | 1.41 | 0.001 | 8.0 | 16.4 | 1.45 | 0.012 | 3.0 | 13.2 | 1.42 | 0.001 | 8.0 | 15.2 | 1.13 | 0.014 | 3.0 | 10.9 |

FIG. 4

Table 5

| Embodiment | Toner number | Charge control agent number | Charge amount (-μC/g) | | | | | | Charge stability (-μC/g) | |
|---|---|---|---|---|---|---|---|---|---|---|
| | | | 1 minute | 2 minute | 5 minute | 10 minute | 20 minute | 60 minute | Initial stage charge amount | Charge amount after storage |
| 59 | 59 | 1-1 | 22.1 | 22.6 | 24.2 | 24.3 | 24.3 | 24.2 | 24.1 | 23.1 |
| 60 | 60 | 1-2 | 22.0 | 23.4 | 23.7 | 24.1 | 24.1 | 24.1 | 24.2 | 23.1 |
| 61 | 61 | 1-3 | 22.1 | 23.1 | 23.5 | 23.7 | 23.7 | 23.7 | 23.7 | 22.4 |
| 62 | 62 | 1-4 | 22.2 | 23.5 | 23.8 | 24.1 | 24.2 | 24.1 | 24.1 | 23.0 |
| 63 | 63 | 1-5 | 23.0 | 23.6 | 24.1 | 24.3 | 24.5 | 24.4 | 24.3 | 23.1 |
| 64 | 64 | 1-6 | 23.1 | 24.0 | 23.1 | 23.2 | 23.2 | 23.2 | 23.1 | 21.2 |
| 65 | 65 | 1-7 | 22.0 | 22.5 | 22.6 | 22.7 | 22.7 | 22.6 | 22.7 | 21.3 |
| 66 | 66 | 1-8 | 21.8 | 22.5 | 22.7 | 22.9 | 23.0 | 23.1 | 22.9 | 21.1 |
| 67 | 67 | 1-9 | 22.0 | 22.9 | 23.5 | 23.8 | 23.9 | 23.8 | 23.8 | 21.2 |
| 68 | 68 | 1-10 | 21.6 | 22.5 | 22.7 | 22.8 | 22.8 | 22.7 | 22.6 | 21.0 |
| 69 | 69 | 1-11 | 21.7 | 22.3 | 22.7 | 22.6 | 22.6 | 22.5 | 22.6 | 20.5 |
| 70 | 70 | 1-12 | 21.8 | 23.0 | 23.5 | 23.6 | 23.7 | 23.7 | 23.5 | 21.3 |
| 71 | 71 | 1-13 | 22.1 | 23.5 | 23.6 | 23.7 | 23.8 | 23.7 | 23.7 | 21.4 |
| 72 | 72 | 1-14 | 21.8 | 22.6 | 23.1 | 23.2 | 23.3 | 23.3 | 23.2 | 21.3 |
| 73 | 73 | 1-15 | 21.2 | 22.9 | 23.5 | 23.7 | 23.7 | 23.6 | 23.7 | 21.4 |
| 74 | 74 | 1-16 | 21.5 | 23.0 | 23.5 | 23.5 | 23.4 | 23.3 | 23.5 | 21.3 |
| 75 | 75 | 1-17 | 21.0 | 22.5 | 23.5 | 23.7 | 23.5 | 23.4 | 23.5 | 21.2 |
| 76 | 76 | 1-18 | 21.0 | 22.4 | 22.5 | 22.6 | 22.4 | 22.4 | 22.6 | 20.5 |
| 77 | 77 | 1-19 | 21.0 | 22.4 | 22.8 | 22.9 | 23.0 | 23.0 | 22.9 | 20.4 |
| 78 | 78 | 1-20 | 21.1 | 22.5 | 22.7 | 22.8 | 22.8 | 22.7 | 22.8 | 20.8 |
| 79 | 79 | 1-21 | 21.4 | 22.9 | 23.5 | 23.6 | 23.6 | 23.5 | 23.6 | 21.4 |
| 80 | 80 | 1-22 | 22.6 | 23.7 | 24.5 | 24.8 | 24.7 | 24.7 | 24.9 | 21.9 |
| 81 | 81 | 1-27 | 22.4 | 23.4 | 23.6 | 23.6 | 23.5 | 23.5 | 23.6 | 21.3 |
| 82 | 82 | 1-30 | 21.7 | 22.5 | 22.9 | 22.9 | 22.9 | 22.8 | 22.9 | 21.1 |
| 83 | 83 | 1-33 | 21.5 | 22.7 | 22.8 | 22.9 | 22.9 | 22.8 | 22.9 | 20.9 |
| 84 | 84 | 1-37 | 23.0 | 24.5 | 24.7 | 25.0 | 25.1 | 25.1 | 25.0 | 23.9 |
| 85 | 85 | 1-38 | 22.9 | 23.7 | 23.9 | 24.0 | 24.0 | 24.1 | 24.0 | 21.9 |
| 86 | 86 | 2-1 | 22.7 | 23.9 | 24.6 | 24.8 | 24.8 | 24.7 | 24.8 | 21.9 |
| 87 | 87 | 2-10 | 22.9 | 23.9 | 24.3 | 24.7 | 24.9 | 24.9 | 24.7 | 22.3 |
| Comp. 7 | Comp. 7 | E-81 | 20.1 | 24.7 | 30.1 | 32.4 | 33.9 | 35.1 | 32.4 | 23.4 |
| Comp. 8 | Comp. 8 | S-34 | 17.6 | 23.5 | 26.8 | 29.0 | 30.3 | 26.5 | 29.0 | 21.0 |
| Comp. 9 | Comp. 9 | E-88 | 10.1 | 15.8 | 19.0 | 24.8 | 27.8 | 30.5 | 24.8 | 15.6 |

FIG. 5

Table 6

| Embodiment | 20°C/50%RH | | | | | | | | 35°C/85%RH | | | | | | | |
|---|---|---|---|---|---|---|---|---|---|---|---|---|---|---|---|---|
| | Initial stage | | | | 500,000 | | | | Initial stage | | | | 500,000 | | | |
| | image density | fog | resolution | Charge amount | image density | fog | resolution | Charge amount | image density | Fog | resolution | Charge amount | image density | fog | resolution | Charge amount |
| 59 | 1.41 | 0.001 | 8.0 | 24.1 | 1.42 | 0.001 | 7.0 | 23.1 | 1.42 | 0.001 | 8.0 | 24.0 | 1.42 | 0.001 | 8.0 | 23.1 |
| 60 | 1.41 | 0.001 | 8.0 | 24.2 | 1.42 | 0.001 | 7.0 | 23.3 | 1.42 | 0.001 | 8.0 | 24.1 | 1.42 | 0.001 | 8.0 | 23.3 |
| 61 | 1.41 | 0.001 | 8.0 | 23.7 | 1.42 | 0.001 | 7.0 | 22.8 | 1.42 | 0.001 | 8.0 | 23.3 | 1.42 | 0.001 | 8.0 | 21.3 |
| 62 | 1.41 | 0.001 | 8.0 | 24.1 | 1.42 | 0.001 | 7.0 | 23.4 | 1.42 | 0.001 | 8.0 | 24.0 | 1.42 | 0.001 | 8.0 | 22.4 |
| 63 | 1.42 | 0.001 | 8.0 | 24.3 | 1.42 | 0.001 | 7.0 | 23.4 | 1.42 | 0.001 | 8.0 | 24.0 | 1.42 | 0.001 | 8.0 | 22.6 |
| 64 | 1.41 | 0.001 | 8.0 | 23.1 | 1.42 | 0.001 | 7.0 | 22.8 | 1.42 | 0.001 | 8.0 | 22.0 | 1.42 | 0.001 | 8.0 | 20.4 |
| 65 | 1.41 | 0.001 | 8.0 | 22.7 | 1.42 | 0.001 | 7.0 | 22.4 | 1.42 | 0.001 | 8.0 | 22.4 | 1.42 | 0.001 | 8.0 | 21.4 |
| 66 | 1.41 | 0.001 | 8.0 | 22.9 | 1.41 | 0.001 | 7.0 | 22.1 | 1.43 | 0.001 | 8.0 | 22.3 | 1.43 | 0.001 | 8.0 | 22.1 |
| 67 | 1.41 | 0.001 | 8.0 | 23.8 | 1.42 | 0.001 | 7.0 | 22.9 | 1.42 | 0.001 | 8.0 | 23.1 | 1.42 | 0.001 | 8.0 | 21.5 |
| 68 | 1.41 | 0.001 | 8.0 | 22.6 | 1.42 | 0.001 | 7.0 | 22.1 | 1.42 | 0.001 | 8.0 | 22.1 | 1.42 | 0.001 | 8.0 | 21.0 |
| 69 | 1.41 | 0.001 | 8.0 | 22.6 | 1.42 | 0.001 | 7.0 | 22.0 | 1.42 | 0.001 | 8.0 | 22.4 | 1.4 | 0.001 | 8.0 | 21.5 |
| 70 | 1.41 | 0.001 | 8.0 | 23.5 | 1.42 | 0.001 | 7.0 | 22.4 | 1.42 | 0.001 | 8.0 | 23.2 | 1.42 | 0.001 | 8.0 | 22.0 |
| 71 | 1.41 | 0.001 | 8.0 | 23.7 | 1.42 | 0.001 | 7.0 | 22.1 | 1.42 | 0.001 | 8.0 | 23.2 | 1.42 | 0.001 | 8.0 | 20.9 |
| 72 | 1.41 | 0.001 | 8.0 | 23.2 | 1.42 | 0.00 | 7.0 | 22.1 | 1.42 | 0.001 | 8.0 | 23.0 | 1.42 | 0.001 | 8.0 | 21.0 |
| 73 | 1.42 | 0.001 | 8.0 | 23.7 | 1.42 | 0.001 | 7.0 | 22.4 | 1.43 | 0.001 | 8.0 | 23.3 | 1.43 | 0.001 | 8.0 | 21.3 |
| 74 | 1.41 | 0.001 | 8.0 | 23.5 | 1.42 | 0.001 | 7.0 | 22.1 | 1.42 | 0.001 | 8.0 | 23.1 | 1.42 | 0.001 | 8.0 | 21.2 |
| 75 | 1.41 | 0.001 | 8.0 | 23.5 | 1.42 | 0.001 | 7.0 | 22.4 | 1.42 | 0.001 | 8.0 | 23.1 | 1.42 | 0.001 | 8.0 | 20.9 |
| 76 | 1.41 | 0.001 | 8.0 | 22.6 | 1.42 | 0.001 | 7.0 | 21.9 | 1.42 | 0.001 | 8.0 | 22.3 | 1.42 | 0.001 | 8.0 | 20.5 |
| 77 | 1.41 | 0.001 | 8.0 | 22.9 | 1.42 | 0.001 | 7.0 | 21.8 | 1.42 | 0.001 | 8.0 | 22.5 | 1.42 | 0.001 | 8.0 | 20.1 |
| 78 | 1.41 | 0.001 | 8.0 | 22.8 | 1.42 | 0.001 | 7.0 | 21.3 | 1.42 | 0.001 | 8.0 | 22.4 | 1.42 | 0.001 | 8.0 | 20.9 |
| 79 | 1.41 | 0.001 | 8.0 | 23.6 | 1.42 | 0.001 | 7.0 | 22.4 | 1.42 | 0.001 | 8.0 | 23.3 | 1.42 | 0.001 | 8.0 | 21.3 |
| 80 | 1.41 | 0.001 | 8.0 | 24.9 | 1.42 | 0.001 | 7.0 | 23.4 | 1.42 | 0.001 | 8.0 | 24.6 | 1.42 | 0.001 | 8.0 | 22.3 |
| 81 | 1.41 | 0.001 | 8.0 | 23.6 | 1.42 | 0.001 | 7.0 | 22.5 | 1.42 | 0.001 | 8.0 | 23.2 | 1.42 | 0.001 | 8.0 | 22.0 |
| 82 | 1.41 | 0.001 | 8.0 | 22.9 | 1.42 | 0.001 | 7.0 | 21.3 | 1.42 | 0.001 | 8.0 | 22.5 | 1.42 | 0.001 | 8.0 | 20.9 |
| 83 | 1.41 | 0.001 | 8.0 | 22.9 | 1.42 | 0.001 | 7.0 | 21.1 | 1.42 | 0.001 | 8.0 | 22.4 | 1.42 | 0.001 | 8.0 | 21.3 |
| 84 | 1.41 | 0.001 | 8.0 | 25.0 | 1.42 | 0.001 | 7.0 | 24.6 | 1.42 | 0.001 | 8.0 | 24.8 | 1.42 | 0.001 | 8.0 | 23.0 |
| 85 | 1.41 | 0.001 | 8.0 | 24.0 | 1.42 | 0.001 | 7.0 | 23.1 | 1.42 | 0.001 | 8.0 | 23.6 | 1.42 | 0.001 | 8.0 | 22.4 |
| 86 | 1.41 | 0.001 | 8.0 | 24.8 | 1.42 | 0.001 | 7.0 | 23.5 | 1.42 | 0.001 | 8.0 | 24.5 | 1.42 | 0.001 | 8.0 | 23.3 |
| 87 | 1.41 | 0.001 | 8.0 | 24.7 | 1.42 | 0.001 | 7.0 | 23.1 | 1.42 | 0.001 | 8.0 | 24.3 | 1.42 | 0.001 | 8.0 | 23.4 |
| Comp.7 | 1.41 | 0.001 | 8.0 | 32.4 | 1.42 | 0.001 | 7.0 | 23.5 | 1.42 | 0.001 | 8.0 | 29.1 | 1.32 | 0.011 | 4.0 | 29.2 |
| Comp.8 | 1.41 | 0.001 | 8.0 | 29.0 | 1.42 | 0.001 | 7.0 | 22.3 | 1.42 | 0.001 | 8.0 | 26.7 | 1.31 | 0.012 | 4.0 | 17.2 |
| Comp.9 | 1.41 | 0.001 | 8.0 | 24.8 | 1.42 | 0.001 | 7.0 | 16.3 | 1.42 | 0.001 | 8.0 | 21.4 | 1.14 | 0.016 | 3.0 | 10.2 |

FIG. 6

Table 7

| Embodiment | Toner number | Charge control agent number | Charge amount (-μC/g) | | | | | | Charge stability (-μC/g) | |
|---|---|---|---|---|---|---|---|---|---|---|
| | | | 1 minute | 2 minute | 5 minute | 10 minute | 20 minute | 60 minute | Initial stage charge amount | Charge amount after storage |
| 88 | 88 | 1-1 | 20.0 | 21.3 | 22.4 | 22.5 | 22.5 | 22.6 | 22.5 | 21.0 |
| 89 | 89 | 1-2 | 20.1 | 21.4 | 21.8 | 22.0 | 21.9 | 21.9 | 22.0 | 20.9 |
| 90 | 90 | 1-3 | 20.1 | 21.4 | 21.7 | 21.9 | 21.9 | 21.8 | 21.9 | 19.8 |
| 91 | 91 | 1-4 | 20.6 | 21.8 | 21.9 | 22.0 | 22.0 | 21.9 | 22.0 | 20.0 |
| 92 | 92 | 1-5 | 21.0 | 21.7 | 22. | 22.1 | 22.4 | 22.4 | 22.1 | 20.1 |
| 93 | 93 | 1-6 | 21.9 | 22.8 | 22.9 | 23.0 | 23.0 | 22.9 | 23.0 | 20.9 |
| 94 | 94 | 1-7 | 19.0 | 10.7 | 21.4 | 21.5 | 21.5 | 21.4 | 21.5 | 19.4 |
| 95 | 95 | 1-8 | 19.8 | 20.2 | 21.0 | 21.1 | 21.1 | 21.2 | 21.1 | 19.4 |
| 96 | 96 | 1-9 | 20.0 | 21.0 | 21.5 | 21.6 | 21.5 | 21.5 | 21.6 | 20.1 |
| 97 | 97 | 1-10 | 19.9 | 20.3 | 20.7 | 20.9 | 21.0 | 21.0 | 20.9 | 19.3 |
| 98 | 98 | 1-11 | 20.0 | 20.9 | 21.0 | 21.1 | 21.2 | 21.2 | 21.1 | 20.0 |
| 99 | 99 | 1-12 | 19.8 | 21.0 | 21.4 | 21.7 | 21.8 | 21.7 | 21.7 | 19.9 |
| 100 | 100 | 1-13 | 20.1 | 21.2 | 22.0 | 22.3 | 22.3 | 22.3 | 22.3 | 20.2 |
| 101 | 101 | 1-14 | 19.8 | 20.7 | 21.3 | 21.3 | 21.3 | 21.3 | 21.3 | 20.3 |
| 102 | 102 | 1-15 | 19.0 | 20.6 | 21.3 | 21.4 | 21.5 | 21.4 | 21.4 | 20.3 |
| 103 | 103 | 1-16 | 19.0 | 21.0 | 21.2 | 21.3 | 21.4 | 21.3 | 21.3 | 20.0 |
| 104 | 104 | 1-17 | 19.1 | 20.7 | 21.1 | 21.2 | 21.3 | 21.4 | 21.2 | 19.5 |
| 105 | 105 | 1-18 | 19.2 | 20.5 | 21.7 | 21.8 | 21.3 | 21.2 | 21.8 | 19.4 |
| 106 | 106 | 1-19 | 19.0 | 20.3 | 20.5 | 20.4 | 20.4 | 20.4 | 20.4 | 19.0 |
| 107 | 107 | 1-20 | 19.0 | 20.3 | 20.5 | 20.6 | 20.5 | 20.5 | 20.6 | 13.0 |
| 108 | 108 | 1-21 | 19.2 | 20.6 | 21.4 | 21.7 | 21.9 | 21.9 | 21.7 | 20.0 |
| 109 | 109 | 1-22 | 20.4 | 21.5 | 22.4 | 22.6 | 22.8 | 22.7 | 22.6 | 20.5 |
| 110 | 110 | 1-27 | 20.3 | 21.2 | 21.7 | 21.9 | 22.1 | 22.1 | 21.9 | 20.1 |
| 111 | 111 | 1-30 | 19.4 | 20.4 | 20.5 | 20.6 | 20.7 | 20.5 | 20.6 | 29.6 |
| 112 | 112 | 1-33 | 19.2 | 20.5 | 21.3 | 21.4 | 21.6 | 21.5 | 21.4 | 20.3 |
| 113 | 113 | 1-37 | 19.3 | 20.9 | 21.6 | 21.8 | 22.0 | 22.0 | 21.8 | 20.3 |
| 114 | 114 | 1-38 | 19.3 | 20.4 | 20.9 | 21.0 | 21.2 | 21.2 | 21.0 | 19.7 |
| 115 | 115 | 2-1 | 20.3 | 21.5 | 21.7 | 21.8 | 21.9 | 21.8 | 21.8 | 20.0 |
| 116 | 116 | 2-10 | 20.1 | 21.6 | 21.9 | 22.1 | 22.5 | 22.5 | 22.1 | 21.0 |
| Comp. 10 | Comp. 10 | E-81 | 15.3 | 22.5 | 27.5 | 30.3 | 33.6 | 29.1 | 30.3 | 19.5 |
| Comp. 11 | Comp. 11 | S-34 | 13.6 | 21.5 | 26.5 | 27.7 | 27.6 | 25.3 | 27.7 | 16.6 |
| Comp. 12 | Comp. 12 | E-88 | 10.0 | 15.4 | 17.3 | 19.3 | 21.6 | 23.1 | 19.3 | 12.1 |

FIG. 7

Table 8

| Embodiment | 20° C/50%RH ||||||||  | 35° C/85%RH ||||||||
|---|---|---|---|---|---|---|---|---|---|---|---|---|---|---|---|---|
| | Initial stage |||| 500,000 |||| | Initial stage |||| 500,000 ||||
| | image density | fog | resolution | Charge amount | image density | fog | resolution | Charge amount | image density | fog | resolution | Charge amount | image density | fog | resolution | Charge amount |
| 88 | 1.42 | 0.001 | 8.0 | 22.5 | 1.42 | 0.001 | 7.0 | 22.5 | 1.42 | 0.001 | 8.0 | 22.2 | 1.42 | 0.001 | 8.0 | 21.0 |
| 89 | 1.41 | 0.001 | 8.0 | 22.0 | 1.42 | 0.001 | 7.0 | 22.0 | 1.42 | 0.001 | 8.0 | 21.8 | 1.42 | 0.001 | 8.0 | 20.0 |
| 90 | 1.42 | 0.001 | 8.0 | 21.9 | 1.42 | 0001 | 7.0 | 21.9 | 1.42 | 0.001 | 8.0 | 21.3 | 1.42 | 0.001 | 8.0 | 19.5 |
| 91 | 1.41 | 0.001 | 8.0 | 22.0 | 1.42 | 0.001 | 7.0 | 22.0 | 1.42 | 0.001 | 8.0 | 21.5 | 1.42 | 0.001 | 8.0 | 19.4 |
| 92 | 1.4 | 0.001 | 8.0 | 22.1 | 1.42 | 0.001 | 7.0 | 22.1 | 1.42 | 0.001 | 8.0 | 26.0 | 1.42 | 0.001 | 8.0 | 14.0 |
| 93 | 1.41 | 0.001 | 8.0 | 23.0 | 1.42 | 0.001 | 7.0 | 23.0 | 1.42 | 0.001 | 8.0 | 22.5 | 1.42 | 0.001 | 8.0 | 20.5 |
| 94 | 1.41 | 0.001 | 8.0= | 21. | 1.42 | 0.001 | 7.0 | 21.5 | 1.43 | 0.001 | 8.0 | 21.0 | 1.43 | 0.001 | 8.0 | 19.4 |
| 95 | 1.42 | 0.001 | 8.0 | 21.1 | 1.42 | 0.001 | 7.0 | 21.1 | 1.42 | 0.001 | 8.0 | 21.4 | 1.42 | 0.001 | 8.0 | 29.5 |
| 96 | 1.41 | 0.001 | 8.0 | 21.6 | 1.42 | 0.001 | 7.0 | 21.6 | 1.42 | 0.001 | 8.0 | 21.1 | 1.42 | 0.001 | 8.0 | 19.2 |
| 97 | 1.41 | 0.001 | 8.0 | 20.9 | 1.42 | 0.001 | 7.0 | 20.9 | 1.42 | 0.001 | 8.0 | 20.3 | 1.42 | 0.001 | 8.0 | 19.0 |
| 98 | 1.41 | 0.001 | 8.0 | 21.1 | 1.42 | 0.001 | 7.0 | 21.1 | 1.42 | 0.001 | 8.0 | 21.0 | 1.42 | 0.001 | 8.0 | 19.4 |
| 99 | 1.41 | 0.001 | 8.0 | 21.7 | 1.42 | 0.001 | 7.0 | 21.7 | 1.42 | 0.001 | 8.0 | 21.3 | 1.42 | 0.001 | 8.0 | 19.3 |
| 100 | 1.42 | 0.001 | 8.0 | 22.3 | 1.42 | 0.001 | 7.0 | 22.3 | 1.42 | 0.001 | 8.0 | 22.1 | 1.42 | 0.001 | 8.0 | 19.3 |
| 101 | 1.41 | 0.001 | 8.0 | 21.3 | 1.42 | 0.001 | 7.0 | 21.3 | 1.42 | 0001 | 8.0 | 21.2 | 1.42 | 0.001 | 8.0 | 19.4 |
| 102 | 1.41 | 0.001 | 8.0 | 21.4 | 1.42 | 0.001 | 7.0 | 21.4 | 1.42 | 0.001 | 8.0 | 21.1 | 1.42 | 0.001 | 8.0 | 19.2 |
| 103 | 1.41 | 0.001 | 8.0 | 21.3 | 1.42 | 0.001 | 7.0 | 21.3 | 1.42 | 0.001 | 8.0 | 21.0 | 1.42 | 0.001 | 8.0 | 19.3 |
| 104 | 1.41 | 0.001 | 8.0 | 21.2 | 1.42 | 0.001 | 7.0 | 21.2 | 1.42 | 0.001 | 8.0 | 20.7 | 1.42 | 0.001 | 8.0 | 19.3 |
| 105 | 1.41 | 0.001 | 8.0 | 21.8 | 1.42 | 0.001 | 7.0 | 21.8 | 1.42 | 0.001 | 8.0 | 21.2 | 1.42 | 0.001 | 8.0 | 19.2 |
| 106 | 1.41 | 0.001 | 8.0 | 20.4 | 1.42 | 0.001 | 7.0 | 20.4 | 1.42 | 0.001 | 8.0 | 20.1 | 1.42 | 0.001 | 8.0 | 18.4 |
| 107 | 1.41 | 0.001 | 8.0 | 20.6 | 1.42 | 0.001 | 7.0 | 20.6 | 1.42 | 0.001 | 8.0 | 20.3 | 1.42 | 0.001 | 8.0 | 18.3 |
| 108 | 1.41 | 0.001 | 8.0 | 21.7 | 1.42 | 0.001 | 7.0 | 21.7 | 1.42 | 0.001 | 8.0 | 21.3 | 1.42 | 0.001 | 8.0 | 19.4 |
| 109 | 1.41 | 0.001 | 8.0 | 22.6 | 1.42 | 0.001 | 7.0 | 22.6 | 1.42 | 0.001 | 8.0 | 22.4 | 1.42 | 0.001 | 8.0 | 21.6 |
| 110 | 1.41 | 0.001 | 8.0 | 21.9 | 1.42 | 0.001 | 7.0 | 21.9 | 1.42 | 0.001 | 8.0 | 21.5 | 1.42 | 0.001 | 8.0 | 20.1 |
| 111 | 1.41 | 0.00 | 8.0 | 20.6 | 1.42 | 0.001 | 7.0 | 20.6 | 1.42 | 0.001 | 8.0 | 20.2 | 1.42 | 0.001 | 8.0 | 19.4 |
| 112 | 1.41 | 0.001 | 8.0 | 21.4 | 1.42 | 0.001 | 7.0 | 21.4 | 1.42 | 0.01 | 8.0 | 21.3 | 1.42 | 0.001 | 8.0 | 19.9 |
| 113 | 1.41 | 0.001 | 8.0 | 21.8 | 1.42 | 0.001 | 7.0 | 21.8 | 1.42 | 0.001 | 8.0 | 21.4 | 1.42 | 0.001 | 8.0 | 19.6 |
| 114 | 1.41 | 0.001 | 8.0 | 21.0 | 1.42 | 0.001 | 7.0 | 21.0 | 1.42 | 0.001 | 8.0 | 20.1 | 1.42 | 0.001 | 8.0 | 18.9 |
| 115 | 1.41 | 0.001 | 8.0 | 21.8 | 1.42 | 0.001 | 7.0 | 21.8 | 1.42 | 0.001 | 8.0 | 21.3 | 1.42 | 0.001 | 8.0 | 19.7 |
| 116 | 1.41 | 0.001 | 8.0 | 22.1 | 1.42 | 0.001 | 7.0 | 22.1 | 1.42 | 0.001 | 8.0 | 21.0 | 1.42 | 0.00 | 8.0 | 19.5 |
| Comp. 10 | 1.41 | 0.001 | 8.0 | 30.3 | 1.37 | 0.011 | 4.0 | 30.3 | 1.42 | 0.001 | 8.0 | 23.1 | 1.31 | 0.015 | 3.0 | 16.5 |
| Comp. 11 | 1.41 | 0.001 | 8.0 | 27.7 | 1.28 | 0.012 | 4.0 | 27.7 | 1.42 | 0.001 | 8.0 | 24.1 | 1.00 | 0.017 | 3.0 | 12.3 |
| Comp. 12 | 1.41 | 0.001 | 8.0 | 19.3 | 1.19 | 0.016 | 4.0 | 19.3 | 1.42 | 0.001 | 8.0 | 16.2 | 1.32 | 0.019 | 2.0 | 10.0 |

FIG. 8

CHARGE CONTROL AGENT AND TONER COMPRISING THE SAME

CROSS-REFERENCE TO RELATED APPLICATIONS

This application claims priority to Chinese Patent Application No. 200710051647.7 filed on Mar. 12, 2007, the contents of which are incorporated herein by reference.

BACKGROUND OF THE INVENTION

1. Field of the Invention

The invention is related to a charge control agent, and the toner containing such charge control agent.

2. Description of the Related Art

Charge control agents mainly comprised of metal complex has been extensively used in various areas, i.e. in the toner used in forming developer for developing an imaging in electrophotographic technology, as a componential material in the making of such toner (see, e.g., Japanese Patent Publication 63-61347, Japanese Patent Publication 2-16916, Japanese Patent Publication 2002-53539, Japanese Patent 2531957, Japanese Patent Publication 7-97530, and Japanese Patent Publication 2005-121776).

The metal complex normally used as charge control agent in toners, including generally known azo-metal complex and salicylate-metal complex.

On one hand, in an imaging forming apparatus using electrophotographic technology to form an imaging, it is necessary to heat the toner imaging recorded on a transfer material in order to fix the imaging. In recent years, for the purpose of energy saving, low temperature fixing is preferred.

However, in the chemical structure of azo-metal complex and salicylate-metal complex, the metal ion often tends to detach from the structure. The result is that in the toners using azo-metal complex or salicylate-metal complex as charge control agent, the detached metal ion may bridge with the resin structure which is another ingredient of the toner. This will cause an increase of the softening point of the toner. Thus high quality imaging in low temperature fixing can not be obtained. In addition, when the environment humidity varies, the imaging quality also varies obviously. These are existing problems.

Thus, there were some suggestions to use metal-free chemicals such as calixarene compounds as a charge control agent for toner. Comparing toners using such charge control agent and toners using metal-complex as charge control agent, the charge characteristics of former are not uniform, and the charge amount of toner particles are not evenly dispersed. The toner particles which are not sufficiently charged will cause the dusting and fogging of toner imaging.

SUMMARY OF THE INVENTION

Based on the above mentioned facts, and the advanced research of the inventors of the invention, it is found that the key problems of traditional charge control agent is uneven crystalline size, high moisture absorption, ill dispersion in resin, and high chance of detachment of metal ion from the chemical structure, etc. To solve these problems and after advanced research, the invention is completed. The purpose of the invention is to provide a charge control agent with excellent charge control property.

Other objects of the invention includes providing a toner with excellent chargeability and capable of providing stably imaging with high quality under any environmental conditions.

A charge control agent comprising a specific type of gallic acid metal complex represented by the following Chemical Formula (1) or Chemical Formula (2) is provided:

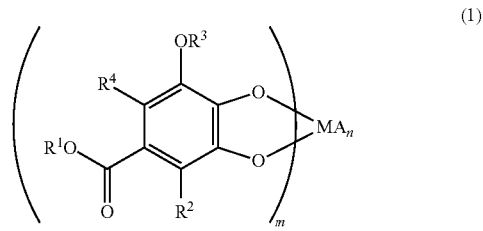

(1)

In the formula (1), $R^1$ represents an alkyl group containing 1-12 carbon atoms, an alkenyl group containing 1-12 carbon atoms, a substituted or unsubstituted aryl group containing 6-12 carbon atoms, or a hydrogen atom; $R^2$ and $R^4$ can independently represent an alkyl group containing 1-12 carbon atoms, an alkenyl group containing 2-12 carbon atoms, an alkoxy group containing 1-12 carbon atoms, a substituted or unsubstituted aryl group containing 6-12 carbon atoms, a halogen atom, or a hydrogen atom; $R^3$ represents an alkyl group containing 1-12 carbon atoms, a substituted or unsubstituted aryl group containing 6-12 carbon atoms, a potassium atom, a sodium atom or a hydrogen atom. M represents a divalent to tetravalent metal atom, A is a counterion, m is a number from 1 to 3, and n is 1 or 2.

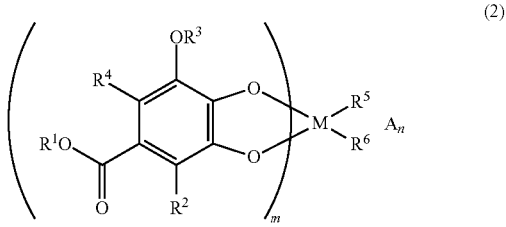

(2)

In the formula (2), $R^1$ represents an alkyl group containing 1-12 carbon atoms, an alkenyl group containing 1-12 carbon atoms, a substituted or unsubstituted aryl group containing 6-12 carbon atoms, or a hydrogen atom; $R^2$ and $R^4$ independently represent an alkyl group containing 1-12 carbon atoms, an alkenyl group containing 2-12 carbon atoms, an alkoxy group containing 1-12 carbon atoms, a substituted or unsubstituted aryl group containing 6-12 carbon atoms, a halogen atom, or a hydrogen atom; $R^3$ represents an alkyl group containing 1-12 carbon atoms, a substituted or unsubstituted aryl group containing 6-12 carbon atoms, a potassium atom, a sodium atom or a hydrogen atom; $R^5$ and $R^6$ independently represent a carboxyl group, a water molecule, or a halogen atom. M represents a divalent to tetravalent metal atom, A is a counterion, m is a number from 1 to 3, and n is 1 or 2.

A toner containing at least a resin, a colorant and a charge control agent is also provided, the charge control agent comprising a specific type of gallic acid metal complex represented by the following Chemical Formula (1) or Chemical Formula (2):

i.

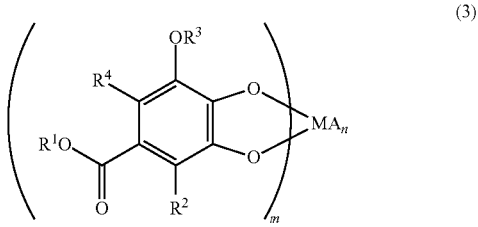

(3)

In the formula (3), $R^1$ represents an alkyl group containing 1-12 carbon atoms, an alkenyl group containing 1-12 carbon atoms, a substituted or unsubstituted aryl group containing 6-12 carbon atoms, or a hydrogen atom; $R^2$ and $R^4$ can independently represent an alkyl group containing 1-12 carbon atoms, an alkenyl group containing 2-12 carbon atoms, an alkoxy group containing 1-12 carbon atoms, a substituted or unsubstituted aryl group containing 6-12 carbon atoms, a halogen atom, or a hydrogen atom; $R^3$ represents an alkyl group containing 1-12 carbon atoms, a substituted or unsubstituted aryl group containing 6-12 carbon atoms, a potassium atom, a sodium atom or a hydrogen atom. M represents a divalent to tetravalent metal atom, A is a counterion, m is a number from 1 to 3, and n is 1 or 2.

ii.

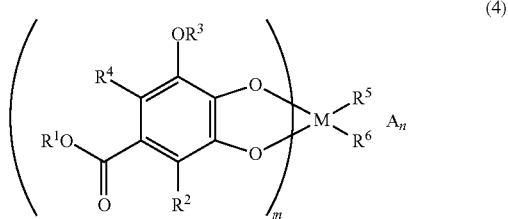

(4)

In the formula (4), $R^1$ represents an alkyl group containing 1-12 carbon atoms, an alkenyl group containing 1-12 carbon atoms, a substituted or unsubstituted aryl group containing 6-12 carbon atoms, or a hydrogen atom; $R^2$ and $R^4$ independently represent an alkyl group containing 1-12 carbon atoms, an alkenyl group containing 2-12 carbon atoms, an alkoxy group containing 1-12 carbon atoms, a substituted or unsubstituted aryl group containing 6-12 carbon atoms, a halogen atom, or a hydrogen atom; $R^3$ represents an alkyl group containing 1-12 carbon atoms, a substituted or unsubstituted aryl group containing 6-12 carbon atoms, a potassium atom, a sodium atom or a hydrogen atom; $R^5$ and $R^6$ independently represent a carboxyl group, a water molecule, or a halogen atom. M represents a divalent to tetravalent metal atom, A is a counterion, m is a number from 1 to 3, and n is 1 or 2.

The charge control agent of the invention which is a gallic acid metal complex has a uniform crystalline size, high charge speed, high thermo stability, low moisture absorption, and good compatibility with resin. Thus excellent charge control property can be obtained.

The charge control agent of the invention is the result of the research of the inventors of the invention, who has found out that traditional charge control agents' disadvantages points include uneven crystalline size, high moisture absorption, ill dispersion in resin, and high chance of detachment of metal ion from the chemical structure, etc. Targeting at these disadvantage points, research has been carried out by the inventors of the invention, which is now completed.

The toner of the invention which contains above mentioned charge control agent with excellent charge control property is capable of providing high quality imaging without any affection by environmental factors. In addition, the excellent charge characteristics of the toner reduce the possibility of dusting and fogging caused by unevenly charged toner particles, thus high quality imaging can be obtained.

Hereafter is a detailed description of the invention.

The charge control agents of the invention includes the chemical compounds shown in the above Chemical Formula (1) (hereafter referred to as 'specific gallic acid metal complex (1)') and the above Chemical Formula (2) (hereafter referred to as 'specific gallic acid metal complex (2)').

In the chemical formula (1) representing 'specific gallic acid metal complex 1', $R^1$ is an alkyl group has 1-12 carbon atoms, a an alkenyl group has 1-12 carbon atoms, a substituted or unsubstituted aryl group containing 6-12 carbon atoms, or a hydrogen atom.

An alkyl group in $R^1$ can be a methyl group, an ethyl group, a propyl group, a butyl group, an octyl group, a 2-ethylhexyl group, a decyl group, or a dodecyl group, etc.

An alkenyl group in $R^1$ can be a 2-propylene group, a 2-octylene group, a 2-decylene group, or a 2-laurylene group, etc.

An aryl group in $R^1$ can be a phenyl group, a 4-toluene group, a 4-tert-butylbenzene group, a 2,6-dimethylbenzene group, a 2,4,6-trimethylbenzene, etc.

In addition, in the chemical formula (1), $R^2$ and $R^4$ independently represent an alkyl group containing 1-12 carbon atoms, an alkenyl alkenyl group containing 2-12 carbon atoms, an alkoxy group containing 1-12 carbon atoms, a substituted or unsbustituted aryl group containing 6-12 carbon atoms, a halogen atom or a hydrogen atom. $R^2$ and $R^4$ can be the same group or different groups.

An alkyl group in $R^2$ and $R^4$ can be a methyl group, an ethyl group, a propyl group, a butyl group, an octyl group, a 2-ethylhexyl group, a decyl group, or a dodecyl group, etc.

An alkenyl group in $R^2$ and $R^4$ can be a 2-propylene group, a 2-octylene group, a 2-decylene group, or a 2-laurylene group, etc.

An alkoxy group in $R^2$ and $R^4$ can be a methoxy group $CH3O-$, an ethoxy group $C2H5O-$, a propoxy group $C3H7O-$, a butoxy group $C4H9O-$, a phenoxy group $C6H13O-$, an octoxy group $C8H17O-$, a decyloxy group $C10H21O-$, a dodecyloxy group $C12H25O-$, etc.

An aryl group in $R^2$ and $R^4$ can be a phenyl group, a 4-toluene group, a 4-tert-butylbenzene group, a 2,6-dimethylbenzene group, a 2,4,6-trimethylbenzene group, etc.

A halogen atom in $R^2$ and $R^4$ can be a chlorine atom, a bromine atom, or an iodine atom, etc.

In addition, in the chemical formula (1), $R^3$ represents an alkyl group containing 1-12 carbon atoms, a substituted or unsubstituted aryl group containing 6-12 carbon atoms, a potassium atom, a sodium atom, or a hydrogen atom.

An alkyl group in $R^3$ can be a methyl group, an ethyl group, a propyl group, a butyl group, an octyl group, a 2-ethylhexyl group, a decyl group, or a dodecyl group, etc.

An aryl group in $R^3$ can be a phenyl group, a 4-toluene group, a 4-tert-butylbenzene group, a 2,6-dimethylbenzene group, a 2,4,6-trimethylbenzene group, etc.

In addition, in the chemical formula (1), M is a divalent to tetravalent metal atom.

The metal atom M can be divalent metal atoms such as Zinc (Zn), Cobalt (Co), Nickel (Ni), or trivalent metal atoms such as Aluminum (Al), Chromium (Cr), Iron (Fe), or tetravalent metal atom such as Zirconium (Zr), etc.

In addition, in the chemical formula (1), A is a counterion.

A counterion group in A can be a hydrogen atom ($H^+$), an ammonium ion ($NH_4^+$), a sodium ion ($Na^+$), a potassium ion ($K^+$), and a calcium ion ($Ca^{2+}$), etc.

Preferred embodiments of specific gallic acid metal complex (1) include the following compounds.

In the chemical formula (1), a compound in which $R^1$, $R^2$, $R^3$ and $R^4$ is a hydrogen atom, M is a chromium atom, A is a sodium ion, m is 2 and n is 1.

In the chemical formula (1), a compound in which $R^1$ is a methyl group, $R^2$, $R^3$ and $R^4$ is a hydrogen atom, M is a chromium atom, A is a sodium ion, m is 2 and n is 1.

In the chemical formula (1), a compound in which $R^1$ is a propyl group, $R^2$, $R^3$ and $R^4$ is a hydrogen atom, M is a chromium atom, A is a sodium ion, m is 2 and n is 1.

In the chemical formula (1), a compound in which $R^1$ is a butyl group, $R^2$, $R^3$ and $R^4$ is a hydrogen atom, M is a chromium atom, A is a sodium ion, m is 2 and n is 1.

In the chemical formula (1), a compound in which $R^1$ is an octyl group, $R^2$, $R^3$ and $R^4$ is a hydrogen atom, M is a chromium atom, A is a sodium ion, m is 2 and n is 1.

In the chemical formula (1), a compound in which $R^1$, $R^2$, $R^3$ and $R^4$ is a hydrogen atom, M is a chromium atom, A is a potassium ion, m is 2 and n is 1.

In the chemical formula (1), a compound in which $R^1$, $R^2$, $R^3$ and $R^4$ is a hydrogen atom, M is a zinc atom, A is a potassium ion, m is 2 and n is 1.

In the chemical formula (1), a compound in which $R^1$ is a propyl group, $R^2$, $R^3$ and $R^4$ is a hydrogen atom, M is a zinc atom, A is a sodium ion, m is 2 and n is 1.

In the chemical formula (1), a compound in which $R^1$ is an octyl group, $R^2$, $R^3$ and $R^4$ is a hydrogen atom, M is a zinc atom, A is a sodium ion, m is 2 and n is 1.

In the chemical formula (1), a compound in which $R^1$, $R^2$, $R^3$ and $R^4$ is a hydrogen atom, M is a zinc atom, A is a sodium ion, m is 2 and n is 1.

In the chemical formula (1), a compound in which $R^1$ is a butyl group, $R^2$, $R^3$ and $R^4$ is a hydrogen atom, M is a zinc atom, A is a sodium ion, m is 2 and n is 1.

In the chemical formula (1), a compound in which $R^1$, $R^2$, $R^3$ and $R^4$ is a hydrogen atom, M is a zirconium atom, A is a sodium ion, m is 3 and n is 1.

In the chemical formula (1), a compound in which $R^1$, $R^2$, $R^3$ and $R^4$ is a hydrogen atom, M is a chromium atom, A is an ammonium ion, m is 2 and n is 1.

In the chemical formula (1), a compound in which $R^1$ is a butyl group, $R^2$, $R^3$ and $R^4$ is a hydrogen atom, M is a zirconium atom, A is a sodium ion, m is 3 and n is 1.

In the chemical formula (1), a compound in which $R^1$ is a butyl group, $R^2$, $R^3$ and $R^4$ is a hydrogen atom, M is a zirconium atom, A is a sodium ion, m is 3 and n is 2.

In the chemical formula (1), a compound in which $R^1$, $R^2$, $R^3$ and $R^4$ is a hydrogen atom, M is an aluminum atom, A is a sodium ion, m is 3 and n is 2.

In the chemical formula (1), a compound in which $R^1$ is an octyl group, $R^2$, $R^3$ and $R^4$ is a hydrogen atom, M is an aluminum atom, A is a sodium ion, m is 3 and n is 2.

In the chemical formula (1), a compound in which $R^1$, $R^2$, $R^3$ and $R^4$ is a hydrogen atom, M is an iron atom, A is a calcium ion, m is 2 and n is 1.

In the chemical formula (1), a compound in which $R^1$ is a propyl group, $R^2$, $R^3$ and $R^4$ is a hydrogen atom, M is an iron atom, A is a sodium ion, m is 2 and n is 1.

In the chemical formula (1), a compound in which $R^1$, $R^2$, $R^3$ and $R^4$ is a hydrogen atom, M is an iron atom, A is a sodium ion, m is 2 and n is 1.

In the chemical formula (1), a compound in which $R^1$ is a decyl group, $R^2$, $R^3$ and $R^4$ is a hydrogen atom, M is an iron atom, A is a sodium ion, m is 2 and n is 1.

In the chemical formula (1), a compound in which $R^1$ is a phenyl group, $R^2$, $R^3$ and $R^4$ is a hydrogen atom, M is a chromium atom, A is a sodium ion, m is 2 and n is 1.

In the chemical formula (1), a compound in which $R^1$ is a phenyl group, $R^2$, $R^3$ and $R^4$ is a hydrogen atom, M is a zirconium atom, A is a sodium ion, m is 3 and n is 1.

In the chemical formula (1), a compound in which $R^1$ is a phenyl group, $R^2$, $R^3$ and $R^4$ is a hydrogen atom, M is a zinc atom, A is a potassium ion, m is 2 and n is 1.

In the chemical formula (1), a compound in which $R^1$ is a phenyl group, $R^2$, $R^3$ and $R^4$ is a hydrogen atom, M is an aluminum atom, A is an ammonium ion, m is 3 and n is 2.

In the chemical formula (1), a compound in which $R^1$ is a 4-methylphenyl group, $R^2$, $R^3$ and $R^4$ is a hydrogen atom, M is an iron atom, A is a calcium ion, m is 1 and n is 1.

In the chemical formula (1), a compound in which $R^1$ and $R^3$ is a hydrogen atom, $R^2$ and $R^4$ is a methyl group, M is a chromium atom, A is a calcium ion, m is 1 and n is 1.

In the chemical formula (1), a compound in which $R^1$ and $R^3$ is a hydrogen atom, $R^2$ and $R^4$ is an octyl group, M is a zinc atom, A is a sodium ion, m is 2 and n is 1.

In the chemical formula (1), a compound in which $R^1$ is a hydrogen atom, $R^2$ and $R^4$ is a dodecyl group, $R^3$ is a methyl group, M is a chromium atom, A is a sodium ion, m is 2 and n is 1.

In the chemical formula (1), a compound in which $R^1$ is a propyl group, $R^2$ and $R^4$ is an ethoxy group, $R^3$ is an ethyl group, M is a chromium atom, A is a sodium ion, m is 2 and n is 1.

In the chemical formula (1), a compound in which $R^1$ is a phenyl group, $R^2$ and $R^3$ is an ethyl group, $R^4$ is an ethoxy group, M is a chromium atom, A is a sodium ion, m is 2 and n is 1.

In the chemical formula (1), a compound in which $R^1$ is a 4-butylphenyl group, $R^2$ and $R^4$ is a hydrogen atom, $R^3$ is a methyl group, M is a chromium atom, A is a sodium ion, m is 2 and n is 1.

In the chemical formula (1), a compound in which $R^1$ is a 4-butylphenyl group, $R^2$ and $R^4$ is a hydrogen atom, $R^3$ is a methyl group, M is a zirconium atom, A is an ammonium ion, m is 3 and n is 1.

In the chemical formula (1), a compound in which $R^1$ is a 4-butylphenyl group, $R^2$ and $R^4$ is a hydrogen atom, $R^3$ is a methyl group, M is a zinc atom, A is a potassium ion, m is 2 and n is 1.

In the chemical formula (1), a compound in which $R^1$ is a 4-butylphenyl group, $R^2$ and $R^4$ is a hydrogen atom, $R^3$ is a methyl group, M is an aluminum atom, A is an ammonium ion, m is 3 and n is 2.

In the chemical formula (1), a compound in which $R^1$ is a 4-butylphenyl group, $R^2$ and $R^4$ is a hydrogen atom, $R^3$ is a methyl group, M is an iron atom, A is a calcium ion, m is 2 and n is 1.

In the chemical formula (1), a compound in which $R^1$ and $R^3$ is a hydrogen atom, $R^2$ and $R^4$ is a chlorine atom, M is a chromium atom, A is a sodium ion, m is 2 and n is 1.

In the chemical formula (1), a compound in which $R^1$ is a propyl group, $R^2$ and $R^4$ is a chlorine atom, $R^3$ is a hydrogen atom, M is a zinc atom, A is a potassium ion, m is 2 and n is 1.

In the chemical formula (1), a compound in which $R^1$ is a propyl group, $R^2$ and $R^4$ is a bromine atom, $R^3$ is a hydrogen atom, M is a zinc atom, A is a sodium ion, m is 2 and n is 1.

In the chemical formula (1), a compound in which $R^1$ is a propyl group, $R^2$ and $R^4$ is a chlorine atom, $R^3$ is an ethyl group, M is a zinc atom, A is a sodium ion, m is 2 and n is 1.

In the chemical formula (2) representing the specific gallic acid metal complex (2), $R^1$ is an alkyl group containing 1-12 carbon atoms, an alkenyl alkenyl group containing 1-12 carbon atoms, a substituted or unsbustituted aryl group containing 6-12 carbon atoms, or a hydrogen atom.

The alkyl group or alkoxy group or aryl group in $R^1$ can be the same as those named in the chemical formula (1) of the specific gallic acid metal complex (1).

In addition, in the chemical formula (2), $R^2$ and $R^4$ independently represent an alkyl group containing 1-12 carbon atoms, an alkenyl group containing 2-12 carbon atoms, an alkoxy group containing 1-12 carbon atoms, a substituted or unsubstituted aryl group containing 6-12 carbon atoms, a halogen atom, or a hydrogen atom. $R^2$ and $R^4$ can be of the same or different type of group.

The alkyl group, alkenyl group, alkoxy group, aryl group or halogen atom in $R^2$ and $R^4$ can be the same as those named in the chemical formula (1) of the specific gallic acid metal complex (1).

In addition, in the chemical formula (2), $R^3$ represents an alkyl group containing 1-12 carbon atoms, a substituted or unsubstituted aryl group containing 6-12 carbon atoms, a potassium atom, a sodium atom or a hydrogen atom.

The alkyl group or the aryl group in $R^3$ can be the same as those named in the chemical formula (1) of the specific gallic acid metal complex (1).

Furthermore, in the chemical formula (2), $R^5$ and $R^6$ independently represent a carboxy group, a water molecule, or a halogen atom. $R^5$ and $R^6$ can be of the same or different type of group.

In addition, in the chemical formula (2), M is a divalent to tetravalent metal atom.

The metal atom M can be the same as those named in the chemical formula (1) of the specific gallic acid metal complex (1).

In addition, in the chemical formula (2), A is a counterion.

The gounterion group in A can be the same as those named in the chemical formula (1) of the specific gallic acid metal complex (1).

The preferred embodiments of the specific gallic acid metal complex (2) include the following compounds:

In the chemical formula (2), a compound in which $R^1$, $R^2$, $R^3$ and $R^4$ is a hydrogen atom, $R^5$ and $R^6$ is a water molecule, M is a cobalt atom, A is a sodium ion, m is 3 and n is 1.

In the chemical formula (2), a compound in which $R^1$ is an octyl group, $R^2$, $R^3$ and $R^4$ is a hydrogen atom, $R^5$ and $R^6$ is a water molecule, M is a cobalt atom, A is a sodium ion, m is 3 and n is 1.

In the chemical formula (2), a compound in which $R^1$ is a phenyl group, $R^2$, $R^3$ and $R^4$ is a hydrogen atom, $R^5$ and $R^6$ is a water molecule, M is a cobalt atom, A is a sodium ion, m is 3 and n is 1.

In the chemical formula (2), a compound in which $R^1$ is a 4-methylphenyl group, $R^2$, $R^3$ and $R^4$ is a hydrogen atom, $R^5$ and $R^6$ is a water molecule, M is a cobalt atom, A is a sodium ion, m is 3 and n is 1.

In the chemical formula (2), a compound in which $R^1$ and $R^3$ is a hydrogen atom, $R^2$ and $R^4$ is a methyl group, $R^5$ and $R^6$ is a water molecule, M is a cobalt atom, A is a sodium ion, m is 3 and n is 1.

In the chemical formula (2), a compound in which $R^1$ and $R^3$ is a hydrogen atom, $R^2$ and $R^4$ is an octyl group, $R^5$ and $R^6$ is a water molecule, M is a cobalt atom, A is a sodium ion, m is 3 and n is 1.

In the chemical formula (2), a compound in which $R^1$ is a hydrogen atom, $R^2$ and $R^4$ is a dodecyl group, $R^3$ is a methyl group, $R^5$ and $R^6$ is a water molecule, M is a cobalt atom, A is a sodium ion, m is 3 and n is 1.

In the chemical formula (2), a compound in which $R^1$ is a propyl group, $R^2$ and $R^4$ is a ethoxy group, $R^3$ is an ethyl group, $R^5$ and $R^6$ is a water molecule, M is a cobalt atom, A is an ammonium ion, m is 3 and n is 1.

In the chemical formula (2), a compound in which $R^1$ is a phenyl group, $R^2$ and $R^3$ is a ethyl group, $R^4$ is an ethoxy group, $R^5$ and $R^6$ is a water molecule, M is a cobalt atom, A is an ammonium ion, m is 3 and n is 1.

In the chemical formula (2), a compound in which $R^1$ is a phenyl group, $R^2$ and $R^3$ is a ethyl group, $R^4$ is an ethoxy group, $R^5$ and $R^6$ is a water molecule, M is a cobalt atom, A is an ammonium ion, m is 3 and n is 1.

In the chemical formula (2), a compound in which $R^1$ and $R^3$ is a hydrogen atom, $R^2$ and $R^4$ is a chlorine atom, $R^5$ and $R^6$ is a water molecule, M is a cobalt atom, A is a sodium ion, m is 3 and n is 1.

In the chemical formula (2), a compound in which $R^1$ is a propyl group, $R^2$ and $R^4$ is a chlorine atom, $R^3$ is a hydrogen atom, $R^5$ and $R^6$ is a water molecule, M is a cobalt atom, A is a sodium ion, m is 3 and n is 1.

In the chemical formula (2), a compound in which $R^1$ is a propyl group, $R^2$ and $R^4$ is a bromine atom, $R^3$ is a hydrogen atom, $R^5$ and $R^6$ is a water molecule, M is a cobalt atom, A is a sodium ion, m is 3 and n is 1.

In the chemical formula (2), a compound in which $R^1$ is a propyl group, $R^2$ and $R^4$ is a chlorine atom, $R^3$ is an ethyl group, $R^5$ and $R^6$ is a water molecule, M is a cobalt atom, A is a sodium ion, m is 3 and n is 1.

The charge control agent composed of the specific gallic acid metal complex (1) and the specific gallic acid metal complex (2) can be prepared by using the following methods.

For embodiment, resolve the gallic acid compounds shown in the chemical formula (3) (hereafter referred to as 'raw gallic acid compound') in water or alcohols to prepare a raw gallic acid compound solution. And the metal ion solution is a solution of chemical compound containing the metal ion which will be used in the metal coordination reaction.

Then, mix the raw metal ion solution containing metal ion for coordination purpose with the raw gallic acid compound solution with a molar ratio of from 1:2 to 1:3. During initial stage of the mixing process, the PH value of the mixture is weak acidic, then while mixing, adjust the pH value to weak basic, and stir under 30° C.-90° C. for 6-27 hours, so that the metal ion coordinates to form metal complex. Such is the production method of preparing the complex.

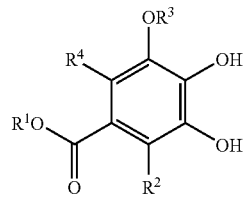

(3)

In this chemical formula, $R^1$ represents an alkyl group containing 1-12 carbon atoms, an alkenyl group containing 1-12 carbon atoms, a substituted or unsubstituted aryl group containing 6-12 carbon atoms, or a hydrogen atom. $R^2$ and $R^4$ independently represent an alkyl group containing 1-12 carbon atoms, an alkenyl group containing 2-12 carbon atoms, an alkoxy group containing 1-12 carbon atoms, a substituted or unsubstituted aryl group containing 6-12 carbon atoms, a halogen atom or a hydrogen atom. $R^3$ represents an alkyl group containing 1-12 carbon atoms, a substituted or unsubstituted aryl group containing 6-12 carbon atoms, a potassium atom, a sodium atom or a hydrogen atom.

During the preparation of the complex, the choices of raw gallic acid compounds and metal ion solution are based on the required type of resultant gallic acid metal complex.

In embodiment, metal ion solution can be such as chromium sulfate solution, chromium formate solution, zinc chloride solution, zinc sulfate solution, chromium tetrachloride solution, aluminum chloride solution, ferric trichloride solution, ferric sulfate solution and zirconium hydroxide, etc.

The alcohols used to prepare raw gallic acid compounds solution are methanol, ethanol, propanol, Ethylene glycol monomethyl ether, Diethylene glycol monoethyl ether, and ethanol absolute, etc.

In addition, the water used to prepare raw gallic acid compounds solution is twice-distilled water.

The pH value adjusting agent to adjust the pH value of raw gallic acid compounds solution and raw metal ion solution to weak acidic at the initial stage. The pH value at the initial stage is above 3, preferred pH value is above 3.5, most preferred 3.5-6.5. If the solution is more acidic than this value, it is difficult to disparate, solubility is reduced, and reaction is inhibited.

At this pH value adjusting stage, the solvent used to obtain the metal ion solution can be hydrochloric acid, sulfuric acid, and nitric acid, etc.

The next stage of the initial mixing is a stage in which raw gallic acid compound solution and metal ion solution is mixed and complexation reaction is under progress. It is necessary to ionize the phalkenyl carboxy group. The pH value of the solution is below 10, the preferred pH value is below 9. The weak basic solution facilitates the ionization of the phalkenyl carboxy group and therefore improves the formation of the complex.

During this stage of pH value adjustment, sodium hydroxide, potassium hydroxide, calcium hydroxide and ammonia can be added into the mixture.

Treat the resultant of the above mentioned complex preparation process with after-treatment such as washing and drying, and obtain the charge control agent of such metal complex from the complex preparation process.

The characteristics of the specific gallic acid metal complex (1) and specific gallic acid metal complex (2) which are the resultant charge control agent of the invention are: uniform crystalline size, high charge speed and high thermo stability, low moisture absorption, and good compatibility with resin. Thus excellent charge control capability is obtained.

In addition, the metal ion coordination in the specific gallic acid complex (1) and the specific gallic acid complex (2) is very strong, which minimize the disengagement of metal ions in the metal complex. Thus in the cases where such charge control agents are used in the toner formula, disadvantages caused by the free metal ion impurity which are disengaged from the structure, such as metal bridging between free metal ion and resin which undermines the toner characteristics and the high fluctuation of imaging quality in various environmental humidity, can be minimized.

The above mentioned charge control agent of the invention can be used as an ingredient of toner as a developer for electrophotography and has very good performance.

In the toner of the invention which adopts as a necessary ingredient the above mentioned specific gallic acid metal complex as charge control agent, it also contains resin and colorant, and optional additives such as release agent which is used to improve fusing property, and other external additives. These apply to both color and monochrome toner.

The resin ingredients here except charge control agent are not limited, all suitable publicly know materials can be adopted.

In embodiment, the resin used can be thermoplastic resin such as styrene acrylic resin, polyester resin, and epoxy resin. These resins can be use separately or in combination.

In addition, colorants include carbon black, magnetite, pigments and dyes.

In addition, release agent can be crystalline materials with low critical surface tension and low melting point, including hydrocarbon wax such as low molecular weight polypropylene, low molecular weight polyethylene, Fischer-Tropsch wax, microcrystalline wax, and paraffin wax, long chain carboxyl acid ester of stearoyl behenate, long chain carboxyl acid ester of pentaerythritol behenate and natural wax such as carnauba wax. The amount used is 1-5% of the total weight of the toner, preferred amount is 2-10% weight.

The amount of charge control agent in the toner of the invention, is 0.1-3 part by weight of every 100 part weight of the toner excluding the weight of the charge control agent, the preferred amount is 0.5-2 part.

In toner where the amount ratio of charge control agent is too small, the chargeability of the toner may be insufficient. On the other hand, when the amount ratio of charge control agent is too big, the charge conductivity of the charge control agent will lead to the leak of charge which prohibits the toner from sufficient charging. At the same time, it might contaminate imaging forming device components such as developer roller sleeve, specificly when the toner is used as a part of duel-component developer, where the carrier is polluted so the toner can not obtaining sufficient charge amount.

The preparation method of toner of the invention is not limited, generally adopted methods such as melting-kneading-pulverization method, suspension polymerization method, emulsion aggregation method and miniemulsion aggregation method and polyester expand method and other publicly know methods can be used.

Due to the high metal coordination force in the charge control agent of the invention, the occurrence of metal ion disengagement is rare. The problem of metal ion bridging in the melting-kneading-pulverization method is not happening thus there is no damage to the fusion property. In addition, the charge control agent has excellent dispersability in resin.

In addition, in methods which polymerization reaction is used, the high metal coordination force in the charge control agent prevents the charge control agent from water adding decomposition during dispersion in the aqueous medium, thus minimize the decomposition of the charge control agent. Further, thanks to the existence of metal coordination binding and ion binding, the dispersability of the charge control agent in aqueous medium is good, and easier to form micro particles of charge control agent. In addition, its dispersability in monomer and solvent is good.

The methods to produce the toner of the invention include those described below: melting-kneading-pulverization method, suspension polymerization method, emulsion aggregation method, miniemulsion method, and polyester expand polymerization method.

Melting-Kneading-Pulverization Method

In the pulverization method, first dry-mix (premixing) the powder of resin, colorant and the charge control agent of the invention and optional release agent, then use equipment such as twin roller extruder to melt and knead the mixture, after cooling pulverize and classify the mixture and obtain the resultant toner. Pulverization can be either mechanical grinding or jet milling.

Emulsion Aggregation and Miniemulsion Aggregation Method

Emulsion aggregation method refers to a preparation method in which resin particles, colorant particles and the particles of the charge control agent of the invention are aggregated and fused to form toner particles. In this method, optional release agent may also be used. In this method, the number average size of the resin particle, colorant particle and the charge control agent particle of the invention preferably is between 50-200 nm. Directly aggregate monomer particles in an aqueous medium by emulsion aggregation reaction or miniemulsion aggregation reaction to form toner particles is a preferred method. In such method, uniform particle can be obtained. The dispersion of colorant particles is achieved by mechanically homogenizing the water-colorant mixture with the presence of surfactant. The homogenizer used can be CLEARMIX or bead miller. The charge control agent of the invention can be dispersed using the same mechanical homogenizer as colorant.

Suspension Polymerization Method

This is a method first mix the monomer, colorant and the charge control agent of the invention and optional release agent, and then using mixer to disperse colorant and the charge control agent of the invention and optional release agent in monomer. Then disperse the mixture in an aqueous medium with disperse stabilizer and form oil drops. After that, initiate the polymerization reaction of the monomer. Remove the disperse stabilizer in the polymerized monomer, and treat it with filtration and drying to obtain toner. In this method, disperse stabilizer is easy to remove. Preferred embodiments include hardly water-soluble inorganic colloid such as calcium phosphate.

Polyester Expand Polymerization Method

Add denatured polyisocyanate, multivalent amine as a molecular elongation agent, a colorant and the charge control agent of the invention in a solvent and mix. Optional release agent may also be used at this time. Disperse the dispersion liquid in an aqueous medium to form oil drops, and heat the mixture to expand the molecule. Then remove the solvent and control the shape of the particle, filtering and drying to obtain toner.

The above mentioned toner of the invention can be used as magnetic or non-magnetic mono-component developer, or mix with carrier to use as duel-component developer.

The colorants used can be carbon black, magnetic materials, dye, and pigment. Carbon black used can be channel black, furnace black, acetylene black, thermal black, and gas black, etc.

The magnetic materials used can be high intensity magnetic materials such as iron, nickel, and cobalt; and compounds of these such as alloy of these metals, ferrite, and magnetite; and metal alloy which does not containing high intensity magnetic metal but can show high magnetism after heat treatment, such as Huesler alloy including manganese-copper-aluminum alloy and manganese-copper-stannum, and chromium dioxide, etc.

In the cases where such toner is used as a magnetic monochrome developer, magnetite may be a suitable black colorants, preferably those number average particle size is within 80-200 nm. The crystalline shape of magnetite can be cubic, spherical, and octahedral. In occasion where a reddish toner is expected, spherical shape magnetite is preferred. In occasion where a bluish toner is expected, cubic shape magnetite is preferred. The amount of magnetic materials used in toner used as magnetic mono-component developer varies as developing method varies. In non-contact developing method, the preferred amount of magnetic material is 35-45% of the total weight of the toner. If the amount used is too small, dusting may occur. On the other hand, over usage of magnetic material may result in inferior developing property.

Dyes used in the toner can be C. I. solvent red 1, solvent red 49, solvent red 52, solvent red 58, solvent red 63, solvent red 111, solvent red 122; C.I. solvent yellow 19, solvent yellow 44, solvent yellow 79, solvent yellow 81, solvent yellow 82, solvent yellow 93, solvent yellow 98, solvent yellow 103, solvent yellow 104, solvent yellow 112, solvent yellow 162; C.I. solvent blue 25, solvent blue 36, solvent blue 60, solvent blue 70, solvent blue 93, solvent blue 95, etc, or a combination of those.

Pigments used in the toner can be C. I. pigment red 5, pigment red 48:1, pigment red 53:1, pigment red 57:1, pigment red 122, pigment red 139, pigment red 144, pigment red 149, pigment red 166, pigment 177, pigment red 178, pigment red 222, pigment red 239; C.I. pigment orange 31, pigment orange 43; C.I. pigment yellow 14, pigment yellow 17, pigment yellow 74, pigment yellow 93, pigment yellow 94, pigment yellow 138, pigment yellow 155, pigment yellow 180, pigment yellow 185; C.I. pigment green 7; C.I. pigment blue 15:3, pigment blue 60, or a combination of those.

The amount of these materials is 2-10% of the total weight of the toner, preferred amount is 3-8%.

The suitable wax that used in the toner of the invention is selected from hydrocarbon wax, ester wax, natural wax, and amide wax.

Hydrocarbon wax includes low molecular weight polyvinyl wax, low molecular weight polypropylene wax, microcrystalline wax, Fischer-Tropsch wax and paraffin wax.

Ester wax includes ester of higher fatty acid and higher alcohols, e.g. behenyl behenate, behenyl stearate, stearoyl stearate, pentaerythritol stearate and pentaerythritol behenate, etc.

Natural wax includes carnauba wax, honey wax, ice wax, etc.

These waxes can be use separately or in a combination of two or more above mentioned types.

The amount of the wax is 2-30% by weight of the total resin particle composition, the preferred amount is 3-25%, and the most preferred amount is 4-20%.

For the purpose of improving fluidity, cleaning property and transfer property, various external additives may be used in the toner of the invention.

The external additives are not explicitly limited. Usable embodiments include inorganic micro particles, organic micro particles, and lubricant.

Embodiments of inorganic micro particles include silicon dioxide, titanium dioxide, and aluminum oxide. Further, these particles are subject to hydrophobicity-imparting treatment by silane coupling agent or titanium coupling agent.

Preferred once number average particle size of these inorganic particles is 5-300 nm. The particle size is determined under SEM×50000, using average number of Feret diameter of 500 particles.

The amount of external additives used in the toner can be 0.1-5.0% of total weight, preferably 0.5-4.0% weight. In addition, external additives can use a combination of above mentioned materials.

Further, viewing from the point of transfer property and cleaning property, metal salt of higher fatty acid may also be used, such as zinc stearate, lithium stearate, or calcium stearate, etc. The amount of such additives is 0.01-0.5% by weight.

In occasion where duel-component developer is used, the carrier in such duel-component toner can select from iron, ferrite, magnetite, or the alloy of these metals with those publicly know metal such as aluminum or lead. Ferrite is a preferred choice. More preferably the alloy does not contain copper and zinc, but containing light alkali metal or light alkaline earth metal's alloy with ferrite. In addition, when using these metals as the core of carrier, it is preferred to coat with the core with silica resin, styrene acrylic resin, acrylic resin, or resin containing florin. The volume average size of the carrier is 30-100 nm.

The above mentioned toner of the invention contains charge control agent which provide excellent charge control property. Thus in the very different environments such as high temperature and high humidity, or low temperature and low humidity, a high imaging quality can be ensured. In addition, due to the excellent tribo-charge ability, there is no possibility of dusting and fogging caused by the unevenly charged toner particles. Thus high quality imaging can be obtained.

In such toner, the ion coupling strength in the gallic acid metal complex which is used as charge control agent is very strong, and that prevents the detachment of metal ion which forms the metal complex. So the problems caused by the free metal ion as an impurity content, such as the bridging between metal ion and resin which destroys the toner property, or large variation of the imaging quality under different environments, can be minimized.

Thus the toner of the invention can provide excellent imaging quality even in low temperature fusing.

BRIEF DESCRIPTION OF THE DRAWINGS

FIGS. 1-8 show tables 1-8, which list physical characteristics of toners in accordance with various embodiments of the invention.

DETAILED DESCRIPTION OF THE INVENTION

The following are embodiments of the invention, but they should not form a limit to the invention.

Embodiment 1 for Preparing Charge Control Agent

Put into a container 20.0% concentration solution containing 20 g chromium sulfate, and use sodium hydroxide and hydrochloric acid to adjust the pH value to 4.5. Dissolve 55 g gallic acid in 200 ml 30.0% ethanol, and adjust the pH value to 8.0 by adding sodium hydroxide. Slowing adding the gallic acid solution into the former solution while stirring, and maintain the pH value of the system at 8.0. React at 50° C. for 12 hours, and filter the resultant crystalline. Wash with ion exchanged water and dry the content, to obtain the reaction resultant (hereafter referred to as charge control agent (1-1)) 57 g.

The resultant charge control agent (1-1) in the Chemical Formula (1), is a gallic acid metal complex in which $R^1$, $R^2$, $R^3$ and $R^4$ are hydrogen atoms, M is a chromium atom, A is sodium, m is 1, and n is 1.

Embodiment 2 for Preparing Charge Control Agent

Put into a container 30.0% concentration solution containing 21 g chromium sulfate, adjust the pH value of the solution with sodium hydroxide and hydrochloric acid to 4.5. While stirring, resolve 59 g of methyl gallate in 200 ml of 50.0% ethanol, and adjust the pH value of this solution to 8.0. Slowly add the methyl gallate solution into the previous solution while use sodium hydroxide to maintain the pH value of the system at 8.0, react at 60° C. for 10 hours. Filter the resultant crystalline and wash with ion exchanged water and drying, to obtain reaction resultant (hereafter referred to as charge control agent (1-2)) 64.5 g.

The resultant charge control agent (1-2) in the Chemical Formula (1), is a gallic acid metal complex in which $R^1$ is a methyl group, $R^2$, $R^3$ and $R^4$ is a hydrogen atom, M is a chromium atom, A is sodium, m is 1, and n is 1.

Embodiment 3 for Preparing Charge Control Agent

Put into a container 20.0% solution of 20 g of chromium sulfate, adjust the pH value of the solution with sodium hydroxide and hydrochloric acid to 3.0. Resolve 63 g of propyl gallate in 250 ml 70.0% ethanol solution; slowly add this solution into the previous solution while stirring. Maintain the pH value of the system at 8.0 with sodium hydroxide and react at 50° C. for 12 hours. Filter the resultant crystalline and wash it with ion exchanged water and drying, to obtain reaction resultant (hereafter referred to as charge control agent (1-3)) 69 g.

The resultant charge control agent (1-3) in the Chemical Formula (1), is a gallic acid metal complex in which $R^1$ is a propyl group, $R^2$, $R^3$ and $R^4$ is a hydrogen atom, M is a chromium atom, A is sodium, m is 1, and n is 1.

Embodiment 4 for Preparing Charge Control Agent

Put into a container 30.0% solution of 19 g of chromium formate, adjust the pH value of the solution with sodium hydroxide and hydrochloric acid to 4.0. Resolve 69 g of butyl gallate in 250 ml of 70.0% ethanol solution, and adjust the pH value with sodium hydroxide to 8.0. While stirring, slowly adding the gallic acid solution into the previous solution, and maintain the pH value of the system at 8.0 using sodium hydroxide. React at 60° C. for 10 hours, filter the resultant crystalline, wash with ion exchanged water and drying, to obtain the reaction resultant (hereafter referred to as charge control agent (1-4)) 73 g.

The resultant charge control agent (1-4) in the Chemical Formula (1), is a gallic acid metal complex in which $R^1$ is a butyl group, $R^2$, $R^3$ and $R^4$ is a hydrogen atom, M is a chromium atom, A is sodium, m is 1 and n is 1.

Embodiment 5 for Preparing Charge Control Agent

Put into a container 30.0% solution of 18 g chromium formate, adjust the pH value of the solution with sodium hydroxide and hydrochloric acid to 4.5. Resolve 56 g of octyl gallate in 300 ml of 70.0% ethanol solution and adjust the pH value to 8.5 with sodium hydroxide. While stirring, slowly add the former solution into this octyl gallate solution, and maintain the system pH value at 8.5. React at 50° C. for 12 hours. Filter the resultant crystalline, wash with ion exchanged water and drying, to obtain the reaction resultant (hereafter referred to as charge control agent (1-5)) 65 g.

The resultant charge control agent (1-5) in the Chemical Formula (1), is a gallic acid metal complex in which $R^1$ is an octyl group, $R^2$, $R^3$ and $R^4$ is a hydrogen atom, M is a chromium atom, A is sodium, m is 1 and n is 1.

Embodiment 6 for Preparing Charge Control Agent

Put into a container 30.0% solution of 19 g of chromium formate and adjust the pH value to 4.5 with potassium hydroxide and hydrochloric acid. Resolve 52 g of gallic acid in 600 ml of twice-distilled water and adjust the pH value to 8.0 with potassium hydroxide, slowly add the gallic acid solution into the previous solution while stirring and maintain the pH value of the system at 8.0 with potassium hydroxide. React at 85° C. for 7 hours, filter the resultant crystalline, wash with ion exchanged water and dry, to obtain reaction resultant (hereafter referred to as charge control agent (1-6)) 47 g.

The resultant charge control agent (1-6) in the Chemical Formula (1) is a gallic acid metal complex in which $R^1$, $R^2$, $R^3$ and $R^4$ is a hydrogen atom, M is a chromium atom, A is potassium, m is 1 and n is 1.

Embodiment 7 for Preparing Charge Control Agent

Put into a container solution of 13 g of zinc chloride. Resolve 38 g of gallic acid in 250 ml of 30.0%-40.0% ethanol solution; adjust the pH value with potassium hydroxide to 8.5. While stirring, slowly add the gallic acid solution into the previous solution, and maintain the pH value of the system at 8.5 with potassium hydroxide. React at 70° C. for 10 hours. Filter the resultant crystalline, wash with ion exchanged water and drying, to obtain reaction resultant (hereafter referred to as charge control agent (1-7)) 39 g.

The resultant charge control agent (1-7) in the Chemical Formula (1) is a gallic acid metal complex in which $R^1$, $R^2$, $R^3$ and $R^4$ is a hydrogen atom, M is a zinc atom, A is potassium, m is 1 and n is 1.

Embodiment 8 for Preparing Charge Control Agent

Put into a container solution of 28 g of zinc sulfate. Resolve 81 g of propyl gallate in 400 ml of 50.0%-60.0% ethanol solution and adjust the pH value of the solution to 8.5 with sodium hydroxide. Slowly add the propyl gallate solution into the previous solution while stirring and maintain the pH value of the system at 8.5. React at 60° C. for 14 hours. Filter the resultant crystalline, wash with ion exchanged water and drying, to obtain reaction resultant (hereafter referred to as charge control agent (1-8)) 77.5 g.

The resultant charge control agent (1-8) in the Chemical Formula (1) is a gallic acid metal complex in which $R^1$ is a propyl group, $R^2$, $R^3$ and $R^4$ is a hydrogen atom, M is a zinc atom, A is sodium, m is 1 and n is 1.

Embodiment 9 for Preparing Charge Control Agent

Put into a container 200 ml solution of 15 g of zinc sulfate. Resolve 60 g of octyl gallate in 350 ml of 30.0%-40.0% ethanol solution; adjust the pH value to 8.5 with sodium hydroxide. Slowly add the octyl gallate solution into the previous solution while stirring, and maintain the pH value of the system with sodium hydroxide at 8.5. React at 75° C. for 16 hours, filter the resultant crystalline, wash with ion exchange water and drying, to obtain reaction resultant (hereafter referred to as charge control agent (1-9)) 59 g.

The resultant charge control agent (1-9) in the Chemical Formula (1) is a gallic metal complex in which $R^1$ is an octyl group, $R^2$, $R^3$ and $R^4$ is a hydrogen atom, M is a zinc atom, A is sodium, m is 1 and n is 1.

Embodiment 10 for Preparing Charge Control Agent

Put into a container 19 g of zinc chloride in 100 ml ethanol solution. Resolve 39 g of gallic acid in 150 ml of ethanol solution and adjust the pH value of the solution to 8.0 with sodium ethylate. React at 50° C. for 18 hours. Filter the resultant crystalline, wash with ion exchanged water and drying, to obtain reaction resultant (hereafter referred to as charge control agent (1-10)) 42 g.

The resultant charge control agent (1-10) in the Chemical Formula (1) is a gallic acid metal complex in which $R^1$, $R^2$, $R^3$ and $R^4$ is a hydrogen atom, M is a zinc atom, A is sodium, m is 1 and n is 1.

Embodiment 11 for Preparing Charge Control Agent

Put into a container 35.0% solution of 14 g of zinc sulfate, adjust the pH value of the solution to 6.0 with sodium hydroxide. Resolve 47 g of butyl gallate in 200 ml of propanol, and slowly adding into the butyl gallate solution into the previous solution with stirring, and maintain the pH value of the system at 8.0 with sodium hydroxide. React at 80° C. for 14 hours, filter the resultant crystalline, wash with 45% acetone and drying, to obtain the reaction resultant (hereafter referred to as charge control agent (1-11)) 48.5 g.

The resultant charge control agent (11) in the Chemical Formula (1) is a gallic metal complex in which $R^1$ is a butyl group, $R^2$, $R^3$ and $R^4$ is a hydrogen atom, M is a zinc atom, A is sodium, m is 1 and n is 1.

Embodiment 12 for Preparing Charge Control Agent

Put into a container water solution of 18 g of zirconium oxychloride octahydrate. Resolve 44 g of gallic acid in 400 ml water and adjust the pH value of the solution to 8.0 with sodium hydroxide. Slowly add the gallic acid solution into the previous solution while stirring, and maintain the pH value of the system at 8.0 with sodium hydroxide. React at 80° C. for 12 hours, filter the resultant crystalline, wash with ion exchanged water and drying, to obtain reaction resultant (hereafter referred to as charge control agent (1-12)) 43 g.

The resultant charge control agent (1-12) in the Chemical Formula (1) is a gallic acid metal complex in which $R^1$, $R^2$, $R^3$ and $R^4$ is a hydrogen atom, M is a zirconium atom, A is sodium, m is 1 and n is 1.

Embodiment 13 for Preparing Charge Control Agent

Put into a container a 23.0% concentration solution containing 47 g of chromium tetrachloride. Resolve 91 g of gallic acid into 200 ml of 50.0%-60.0% ethanol and adjust the pH value to 8.0 with ammonia. Slowly add the gallic acid solution into the previous solution while stirring, and maintain the pH value of the system at 8.0 with ammonia. React at 60° C. for 10 hours, filter the resultant crystalline, wash with ion exchanged water and drying, to obtain reaction resultant (hereafter referred to as charge control agent (1-13)) 87 g.

The resultant charge control agent (1-13) in the Chemical Formula (1) is a gallic acid metal complex in which $R^1$, $R^2$, $R^3$ and $R^4$ is a hydrogen atom, M is a chromium atom, A is an ammonium ion, m is 1, and n is 1.

Embodiment 14 for Preparing Charge Control Agent

Put into a container 25 g of zirconium oxychloride octahydrate resolved in 250 ml of water. Resolve 49 g of butyl gallate into 1750 ml of 75.0% ethanol and adjust the pH value to 8.0 with 25% concentration ammonia. Slowly add the butyl gallate solution into the previous solution while stirring, and maintain the pH value of the system at 8.0 with 25% concentration ammonia. React at 55° C. for 7 hours, filter the resultant crystalline, wash with ion exchanged water and drying, to obtain reaction resultant (hereafter referred to as charge control agent (1-14)) 47 g.

The resultant charge control agent (1-14) in the Chemical Formula (1) is a gallic acid metal complex in which $R^1$ is a butyl group, $R^2$, $R^3$ and $R^4$ is a hydrogen atom, M is a zirconium atom, A is an ammonium ion, m is 1, and n is 1.

Embodiment 15 for Preparing Charge Control Agent

Put into a container a 20.0% concentration solution containing 13.5 g of aluminum chloride, adjust the pH value to 4.0 with sodium hydroxide and hydrochloric acid. Resolve 63 g of propyl gallate in 200 ml of water. Slowly add the propyl gallate solution into the previous solution while stirring, and maintain the pH value of the system at 3.0 with sodium hydroxide and hydrochloric acid. React at 70° C. for 24 hours, filter the resultant crystalline, wash with ion exchanged water and drying, to obtain reaction resultant (hereafter referred to as charge control agent (1-15)) 62 g.

The resultant charge control agent (1-15) in the Chemical Formula (1) is a gallic acid metal complex in which $R^1$ is a propyl group, $R^2$, $R^3$ and $R^4$ is a hydrogen atom, M is a aluminum atom, A is sodium, m is 1, and n is 2.

Embodiment 16 for Preparing Charge Control Agent

Put into a container a 25.0% concentration solution containing 28 g of aluminum chloride, adjust the pH value to 3.5 with sodium hydroxide and hydrochloric acid. Resolve 91 g of gallic acid in 700 ml of water and adjust the pH value to 3.5 with sodium hydroxide and hydrochloric acid. Slowly add the gallic acid solution into the previous solution while stirring, and maintain the PH value of the system at 3.5 with sodium hydroxide and hydrochloric acid. React at 75° C. for 24 hours, filter the resultant crystalline, wash with ion exchanged water and drying, to obtain reaction resultant (hereafter referred to as charge control agent (1-16)) 87 g.

The resultant charge control agent (1-16) in the Chemical Formula (1) is a gallic acid metal complex in which $R^1$, $R^2$, $R^3$ and $R^4$ is a hydrogen atom, M is a aluminum atom, A is sodium, m is 1, and n is 2.

Embodiment 17 for Preparing Charge Control Agent

Put into a container a 25.0% concentration solution containing 17 g of aluminum sulfate, and adjust the pH value to 3.5 with sodium hydroxide and hydrochloric acid. Resolve 62 g of octyl gallate in 500 ml of 70.0% ethanol solution and adjust the pH value to 3.5 with sodium hydroxide and hydrochloric acid. Slowly add the propyl gallate solution into the previous solution while stirring, and maintain the pH value of the system at 3.5 with sodium hydroxide and hydrochloric acid. React at 75° C. for 24 hours, filter the resultant crystalline, wash with ion exchanged water and drying, to obtain reaction resultant (hereafter referred to as charge control agent (1-17)) 67 g.

The resultant charge control agent (1-17) in the Chemical Formula (1) is a gallic acid metal complex in which $R^1$ is an octyl group, $R^2$, $R^3$ and $R^4$ is a hydrogen atom, M is a aluminum atom, A is sodium, m is 1, and n is 2.

Embodiment 18 for Preparing Charge Control Agent

Put into a container 200 ml water solution containing 16 g of ferric trichloride. Resolve 48 g of gallic acid in 250 ml of water. Slowly add the gallic acid solution into the previous solution while stirring, and maintain the pH value of the system at 6.0 with calcium hydroxide and hydrochloric acid. React at 65° C. for 10 hours, filter the resultant crystalline, wash with ion exchanged water and drying, to obtain reaction resultant (hereafter referred to as charge control agent (1-18)) 52 g.

The resultant charge control agent (1-18) in the Chemical Formula (1) is a gallic acid metal complex in which $R^1$, $R^2$, $R^3$ and $R^4$ is a hydrogen atom, M is an iron atom, A is calcium, m is 3, and n is 1.

Embodiment 19 for Preparing Charge Control Agent

Put into a container a 45.0% concentration solution containing 19 g of ferric sulfate. Resolve 49 g of propyl gallate in 350 ml of 75.0% concentration ethanol solution and adjust the pH value to 6.0 with sodium hydroxide and hydrochloric acid. Slowly add the propyl gallate solution into the previous solution while stirring, and maintain the pH value of the system at 6.0 with sodium hydroxide and hydrochloric acid. React at 60° C. for 12 hours, filter the resultant crystalline, wash with ion exchanged water and drying, to obtain reaction resultant (hereafter referred to as charge control agent (1-19)) 62 g.

The resultant charge control agent (1-19) in the Chemical Formula (1) is a gallic acid metal complex in which $R^1$ is a propyl group, $R^2$, $R^3$ and $R^4$ is a hydrogen atom, M is an iron atom, A is sodium, m is 3, and n is 1.

Embodiment 20 for Preparing Charge Control Agent

Put into a container a solution of 17 g of ferric trichloride in 200 ml of ethanol absolute. Resolve 51 g of gallic acid in 300 ml of ethanol absolute. Slowly add the gallic acid solution into the previous solution while stirring, and maintain the pH value of the system at 6.0 with sodium ethalyte. React at 50° C. for 12 hours, filter the resultant crystalline, wash with ethanol absolute and drying, to obtain reaction resultant (hereafter referred to as charge control agent (20)) 53 g.

The resultant charge control agent (1-20) in the Chemical Formula (1) is a gallic acid metal complex in which $R^1$, $R^2$, $R^3$ and $R^4$ is a hydrogen atom, M is an iron atom, A is sodium, m is 3, and n is 1.

Embodiment 21 for Preparing Charge Control Agent

Put into a container a 28.0% concentration ethanol solution of 17 g of ferric trichloride. Resolve 53 g of propyl gallate in 250 ml of ethanol solution containing 10% sodium ethalyte. Slowly add the gallic acid solution into the previous solution while stirring, and maintain the pH value of the system at 6.0. React at 70° C. for 12 hours, filter the resultant crystalline, wash with 50.0% ethanol and drying, to obtain reaction resultant (hereafter referred to as charge control agent (1-21)) 57 g.

The resultant charge control agent (1-21) in the Chemical Formula (1) is a gallic acid metal complex in which $R^1$ is a propyl group, $R^2$, $R^3$ and $R^4$ is a hydrogen atom, M is an iron atom, A is sodium, m is 3, and n is 1.

Embodiment 22 for Preparing Charge Control Agent

Put into a container a 20.0% concentration solution of 20 g of chromium sulfate and adjust the pH value of the solution to 4.5 with sodium hydroxide and hydrochloric acid. Resolve 63 g of phenyl gallate in 200 ml of 30.0% concentration ethanol and adjust the pH value to 8.0 with sodium hydroxide. Slowly add the phenyl gallate solution into the previous solution while stirring, and maintain the pH value of the system at 8.0 with sodium hydroxide. React at 50° C. for 12 hours, filter the resultant crystalline, wash with ion exchanged water and drying, to obtain reaction resultant (hereafter referred to as charge control agent (1-22)) 57 g.

The resultant charge control agent (1-22) in the Chemical Formula (1) is a gallic acid metal complex in which $R^1$ is a phenyl group, $R^2$, $R^3$ and $R^4$ is a hydrogen atom, M is a chromium atom, A is sodium, m is 1, and n is 1.

Embodiment 23 for Preparing Charge Control Agent

Put into a container a 20.0% concentration solution of 20 g of chromium sulfate and adjust the pH value of the solution to 4.5 with sodium hydroxide and hydrochloric acid. Resolve 60 g of derivative of gallic acid in which $R^2$ and $R^4$ are substituted by a methyl group in 200 ml of 30.0% concentration ethanol and adjust the pH value to 8.0 with sodium hydroxide. Slowly add the gallic acid derivative solution into the previous solution while stirring, and maintain the pH value of the system at 8.0 with sodium hydroxide. React at 50° C. for 12 hours, filter the resultant crystalline, wash with ion exchanged water and drying, to obtain reaction resultant (hereafter referred to as charge control agent (1-27)) 52 g.

The resultant charge control agent (1-27) in the Chemical Formula (1) is a gallic acid metal complex in which $R^1$ and $R^3$ is a hydrogen atom, $R^2$ and $R^4$ is a methyl group, M is a chromium atom, A is sodium, m is 1, and n is 1.

Embodiment 24 for Preparing Charge Control Agent

Put into a container a 20.0% concentration solution of 20 g of chromium sulfate and adjust the pH value of the solution to 4.5 with sodium hydroxide and hydrochloric acid. Resolve 82 g of derivative of gallic acid in which $R^1$ is substitute by a propyl group, $R^3$ is substituted by an ethyl group, $R^2$ and $R^4$ are substituted by an oxyethyl group in 200 ml of 30.0% concentration ethanol and adjust the pH value to 8.0 with sodium hydroxide. Slowly add the gallic acid derivative solution into the previous solution while stirring, and maintain the pH value of the system at 8.0 with sodium hydroxide. React at 60° C. for 15 hours, filter the resultant crystalline, wash with ion exchanged water and drying, to obtain reaction resultant (hereafter referred to as charge control agent (1-30)) 85 g.

The resultant charge control agent (1-30) in the Chemical Formula (1) is a gallic acid metal complex in which $R^1$ is a propyl group, $R^3$ is an ethyl group, $R^2$ and $R^4$ is an oxyethyl group, M is a chromium atom, A is sodium, m is 1, and n is 1.

Embodiment 25 for Preparing Charge Control Agent

Put into a container a solution of 15 g of zirconium oxychloride octahydrate in 250 ml of water. Resolve 79 g of derivative of gallic acid in which $R^1$ is substitute by a 4-butylphenyl group, $R^3$ is substituted by a methyl group in 175 ml of 75.0% concentration methanol and adjust the pH value to 8.0 with 25.0% concentration ammonia solution. Slowly add the gallic acid derivative solution into the previous solution while stirring, and maintain the pH value of the system at 8.0 with 25.0% concentration ammonia solution. React at 55° C. for 7 hours, filter the resultant crystalline, wash with ion exchanged water and drying, to obtain reaction resultant (hereafter referred to as charge control agent (1-33)) 82 g.

The resultant charge control agent (1-33) in the Chemical Formula (1) is a gallic acid metal complex in which $R^1$ is a butylphenyl group, $R^3$ is a methyl group, $R^2$ and $R^4$ is a hydrogen group, M is a zirconium atom, A is an ammonium ion, m is 1, and n is 1.

Embodiment 26 for Preparing Charge Control Agent

Put into a container a 20.0% concentration solution of 20 g of chromium sulfate and adjust the pH value to 4.5 with sodium hydroxide and hydrochloric acid. Resolve 60 g of derivative of gallic acid in which $R^2$ and $R^4$ are substituted by a chlorine group in 200 ml of 30.0% concentration ethanol and adjust the pH value to 8.0 with sodium hydroxide. Slowly add the gallic acid derivative solution into the previous solution while stirring, and maintain the pH value of the system at 8.0 with sodium hydroxide. React at 60° C. for 12 hours, filter the resultant crystalline, wash with ion exchanged water and drying, to obtain reaction resultant (hereafter referred to as charge control agent (1-37)) 62 g.

The resultant charge control agent (1-37) in the Chemical Formula (1) is a gallic acid metal complex in which $R^1$ and $R^3$ is a hydrogen atom, $R^2$ and $R^4$ is a chlorine group, M is a chromium atom, A is sodium, m is 1, and n is 1.

Embodiment 27 for Preparing Charge Control Agent

Put into a container a 35.0% concentration solution of 14 g of zinc sulfate and adjust the pH value to 6.0 with sodium hydroxide. Resolve 69 g of derivative of gallic acid in which $R^1$ is substituted by a propyl group, $R^2$ and $R^4$ are substituted by a chlorine group in 200 ml of propanol. Slowly add the gallic acid derivative solution into the previous solution while stirring, and maintain the pH value of the system at 8.0 with sodium hydroxide. React at 80° C. for 18 hours, filter the resultant crystalline, wash with 45.0% concentration propanol and drying, to obtain reaction resultant (hereafter referred to as charge control agent (1-38)) 48.5 g.

The resultant charge control agent (1-38) in the Chemical Formula (1) is a gallic acid metal complex in which $R^1$ is a propyl group, $R^2$ and $R^4$ is a chlorine group, $R^3$ is a hydrogen atom, M is a zinc atom, A is sodium, m is 1, and n is 1.

Embodiment 28 for Preparing Charge Control Agent

Put into a container a 20.0% concentration solution of 22 g of cobalt trichloride and adjust the pH value to 5.0 with sodium hydroxide and hydrochloric acid. Resolve 55 g of gallic acid in 200 ml of 30.0% concentration ethanol and adjust the pH value to 8.0 with sodium hydroxide. Slowly add the gallic acid solution into the previous solution while stirring, and maintain the pH value of the system at 8.0 with sodium hydroxide. React at 60° C. for 15 hours, filter the resultant crystalline, wash with ion exchanged water and drying, to obtain reaction resultant (hereafter referred to as charge control agent (2-1)) 57 g.

The resultant charge control agent (2-1) in the Chemical Formula (2) is a gallic acid metal complex in which $R^1$, $R^2$, $R^3$ and $R^4$ is a hydrogen atom, $R^5$ and $R^6$ is a water molecule, M is a cobalt atom, A is sodium, m is 1, and n is 1.

Embodiment 29 for Preparing Charge Control Agent

Put into a container a 20.0% concentration solution of 22 g of cobalt trichloride and adjust the pH value to 5.0 with sodium hydroxide and hydrochloric acid. Resolve 79 g of gallic acid derivative in which $R^1$ is substituted by a 4-butylphenyl group and $R^3$ is substituted by a methyl group in 200 ml of 30.0% concentration ethanol and adjust the pH value to 8.0 with sodium hydroxide. Slowly add the gallic acid solution into the previous solution while stirring, and maintain the pH value of the system at 8.0 with sodium hydroxide. React at 55° C. for 12 hours, filter the resultant crystalline, wash with ion exchanged water and drying, to obtain reaction resultant (hereafter referred to as charge control agent (2-10)) 79 g.

The resultant charge control agent (2-10) in the Chemical Formula (2) is a gallic acid metal complex in which $R^1$ is a 4-butylphenyl group, $R^2$ and $R^4$ is a hydrogen atom, $R^3$ is a methyl group, $R^5$ and $R^6$ is a water molecule, M is a cobalt atom, A is sodium, m is 1, and n is 1.

The charge control agents obtained from the preparation embodiment 1 to preparation embodiment 29 are used to making toner according to the following methods, and the obtained toner is further made into developer.

Embodiment 1 for Preparing Pulverized Toner

Mix 1 part of charge control agent (1-1), 100 parts of styrene-acrylic resin (styrene: butyl acrylate: methyl methacrylate=70:20:5 (by weight), softening point is 128° C.), 8 parts of carbon black 'MOGUL L' (manufactured by Cabot. Co) and 6 parts of low molecular weight polypropylene '660P' (manufactured by Sanyo Chemical) in a Henschel mixer. Melt and knead the resultant mixture with twin-screw extruder, after cooling down, pulverize with a jet mill and classify with cyclone classifier, to obtain colored particles with a volume average diameter about 8.5 mm.

Then add 0.8 parts of 67% hydrophobic silica dioxide which number average diameter is 12 nm into every 100 parts of the colored particles. Mix with a Henschel mixer to obtain the toner.

Embodiments 2-29 for Preparing Pulverized Toner and Comparative Embodiments 1-3 for Preparing Pulverized Toners In the embodiment for preparing pulverized toner 1, use the charge control agents listed in table 1 to replace the charge control agent (1-1), and other conditions are the same with that in the preparation of pulverized toner 1, to obtain toner.

Hereafter, the pulverized toners from using charge control agents (1-1) to charge control agent (2-10) listed in the table 1 are named toner (1)-toner (29). In addition, use chromium salicylate complex E-81 (manufactured by Orient Chemical Co), calixarene derivative E-88 (manufactured by Orient Chemical Co), and chromium azo complex S-34 (manufactured by Orient Chemical Co) as comparative charge control agents, to obtain comparative pulverized toner, as shown in table 1, which are named comparative toner (1)-comparative toner (3).

Embodiment for Preparing Toner with Suspension Polymerization Method

Mix 1 part of charge control agent, 75 parts of styrene monomer, 25 parts of butylacrylate, 5 parts of MOGUL L, 3 parts of copper phthalocyanine pigment (C.I. P.B. 15:3) and 2 parts of Azobis (isovaleronitrile). Disperse in sand mill at 10,000 rpm for 30 minutes to obtain a mixture of polymerizable monomer.

Then, add 600 parts of ion exchanged water and 500 parts of 0.1 mol/L $Na_3PO_4$ water solution in a 2 L flask with 4 necks equipped with high speed mixing device TK homogenizer (manufactured by PRIMIX Corporation) and baffleplate, mix at 12,000 rpm at 65° C. Slowly add 70 parts of 1.0 mol/L CaCl water solution to prepare a aqueous dispersion medium containing micro hardly water soluble dispersant $Ca_3(PO_4)_2$.

Then, add the polymerizable monomer mixture into the aqueous water dispersion medium, in nitrogen gas environment under 65° C., keep stirring at 12,000 rpm for 15 minutes to form particles of the polymerizable monomer composite. Change the stirring blade to spiral stirring blade and by the stirring speed and the angle of the baffleplate to control the shape of the particles. Maintain the temperature for 10 hours to complete the polymerization.

After the completion of the polymerization, cool down the suspension liquid, add diluted hydrochloric acid to remove dispersant. Wash with water for multiple times, and dry, to obtain colored particles with a volume average diameter of 8.2 μm.

Then add 0.8 parts of 67% hydrophobic silica dioxide which number average diameter is 12 nm into every 100 parts of the colored particles. Mix with a Henschel mixer to obtain the toner.

Embodiments 2-29 for Preparing Suspension Polymerized Toners and Comparative Embodiments 1-3 for Preparing Suspension Polymerized Toners In the example for preparing suspension polymerized toner 1, use the charge control agents listed in table 3 to replace the charge control agent (1-1), and other conditions are the same with that in the preparation of suspension polymerized toner 1, to obtain toner.

Hereafter, the suspension polymerized toners from using charge control agents (1-1) to charge control agent (2-10) listed in the table 3 are named toner (30)-toner (58). In addition, use chromium salicylate complex E-81 (manufactured by Orient Chemical Co), calixarene derivative E-88 (manufactured by Orient Chemical Co), and chromium azo complex S-34 (manufactured by Orient Chemical Co) as comparative charge control agents, to obtain comparative suspension polymerized toner, as shown in table 1, which are named comparative toner (4)-comparative toner (6).

Embodiments for Preparing Toner with Emulsion Aggregation Method

Preparing the dispersion liquid of resin particles

Add into a reactor with stirring device, temperature sensor, cooling tube and nitrogen injector a solution of 16 parts of sodium dodecylsulfate in 1500 parts of ion exchanged water. Under nitrogen gas current stir at 230 rpm, and heat the system to 80° C. Then, add a solution of 5 parts of potassium persulfate in 100 parts of ion exchanged water into the system, heat the system again to 80° C. In one hour drop into the reactor a polymerizable monoer liquid which contains 350 parts of styrene, 125 parts of n-butylacrylate, 25 parts of methacrylic acid and 4 parts of n-dodecanethiol. Heat to 80° C. for 2 hours, and mix to polymerize, to prepare resin particle dispersion liquid (1).

Use the electrophoresis light scattering photometer (ELS-800) (Manufactured by Osuka Electronics Co., Ltd.) to determine the particle size in the resin particle dispersion liquid (1), the volume average diameter of which is 110 nm.

2) Preparing Carbon Black Dispersion Liquid

Resolve 10 parts of sodium dodecylsulfate in 160 parts of ion exchanged water. Slowly add 40 parts of carbon black 'MOGUL L' (manufactured by CABOT, CO.) into the solution, disperse with 'CLEARMIX' (manufactured by M Technique CO.), to prepare colorant dispersion liquid (1).

Use the electrophoresis light scattering photometer (ELS-800) (Manufactured by Osuka Electronics Co., Ltd.) to determine the particle size in the colorant dispersion liquid (1), the volume average diameter of which is 120 nm.

3) Preparing Charge Control Agent Dispersion Liquid

Resolve 5 parts of sodium dodecylsulfate in 200 parts of ion exchanged water. Slowly add 5 parts of charge control agent (1-1) into the solution. Disperse with sand mill to prepare a charge control agent dispersion liquid (1).

Use the electrophoresis light scattering photometer (ELS-800) (Manufactured by Osuka Electronics Co., Ltd.) to determine the particle size is 110 nm.

4) Preparing Release Agent Dispersion Liquid

Heat the solution of 6 parts of sodium sulfate in 200 parts of ion exchanged water to 90° C., while stirring, slowly add 40 parts of melted 90° C. carnauba wax, treat with sonication to disperse and form wax dispersion liquid (1).

Use the electrophoresis light scattering photometer (ELS-800) (Manufactured by Osuka Electronics Co., Ltd.) to determine the particle size is 130 nm.

5) Aggregating (Fusing) with Resin Particle

Add into a reactor with stirring device, temperature sensor, cooling tube and nitrogen injector the above mentioned resin particle dispersion liquid, colorant dispersion liquid, charge control agent dispersion liquid, release agent, disperse agent and 1400 parts of ion exchanged water, and add into this mixture a solution of 10 parts of polyoxyethylene-2-sodium dodecylsulfate ether in 500 parts of ion exchanged water. Adjust the temperature of the system to 30° C., and adjust the pH value to 10 with 5N sodium hydroxide water solution.

Then resolve 100 parts of magnesium chloride in 100 parts of ion exchanged water and add into the mixture at 30° C. during 10 minutes under continuous stirring. Keep stirring for further 3 minutes and heat the system to 90° C. over 60 minutes. Keep the temperature at 90° C. to let the particles aggregate. Use 'Coulter Multilizer III to determine the size of aggregated particle. When the desired particle size is obtained, add a solution of 300 parts of sodium chloride in 1000 parts of ion exchanged water to stop particle growth. Heat the mixture to 98° C. to let the particle fuse until test with 'FPIA-2100' the average roundness of the particles is 0.965. Cool the liquid to 30° C., adjust the pH value to 4.0 with hydrochloric acid, and stop stirring, to obtain toner.

Embodiments 2-29 for Preparing Emulsion Aggregated Toners and Comparative Embodiments 1-3 for Preparing Emulsion Aggregated Toners In the example for preparing emulsion aggregated toner 1, use the charge control agents listed in table 5 to replace the charge control agent (1-1), and other conditions are the same with that in the preparation of emulsion aggregated toner 1, to obtain toner.

Hereafter, the emulsion aggregated toners from using charge control agents (1-1) to charge control agent (2-10) listed in the table 1 are named toner (59)-toner (87). In addition, use chromium salicylate complex E-81 (manufactured by Orient Chemical Co), calixarene derivative E-88 (manufactured by Orient Chemical Co), and chromium azo complex S-34 (manufactured by Orient Chemical Co) as comparative charge control agents, to obtain comparative emulsion aggregated d toner, as shown in table 5, which are named comparative toner (7)-comparative toner (9).

Embodiment for Preparing Toner with Polyester Expand Polymerization Method

Preparation of Denatured Polyisocyanate

Add into a reactor with mixing and nitrogen injection device 724 parts of bisphalkenyl A ethylene oxide 2 mol additive, 200 parts of isophthalic acid, 70 parts of fumaric acid, and 2 parts of dibutylin oxide. React under 230° C. and normal pressure for 8 hours, and under 12 mm Hg for 5 hours. Cool the system to 160° C., add 32 parts of phthalic anhydride, react for 2 hours to obtain polyester al. The unformed polyester al has a glass transition point of 59° C., and a softening point of 121° C., the number average molecular weight (Mn) is 6,000, and the weight average molecular weight (Mw) is 28,000.

Then add to every 1,000 parts of the unformed polyester al 2,000 parts of ethyl acetate, and 120 parts of isophorone diisocyanate. React at 80° C. for 2 hours and obtain denatured polyisocyanate 1.

Put in a reactor with hydraulic seal and stirrer 450 parts of ethyl acetate, 300 parts of denatured polyisocyanate 1, 14 parts of isophoronediamine, 4 parts of copper phthalocyanine blue, 4 parts of carbon black, 15 parts of carnauba wax, 3 parts of charge control agent (1-1), and react under 20° C. for 2 hours to obtain toner composite 1.

At the same time, Put into another reactor 600 parts of ion exchanged water, 60 parts of methyl ethyl ketone, 60 parts of tricalcium phosphate, 0.3 parts of Sodium dodecyl benzene sulfonate. Stir with TK homogenizer (manufactured by PRIMIX Corporation) at 15,000 rpm under 30° C. for 3 minutes. Add this mixture to the aqueous dispersion liquid of the above mentioned toner composite 1, heat to 80° C., and treat with urea for 10 hours to obtain particles with a volume average diameter of 5.5 μm.

Move the urea-treated toner composite 1 to another mixer, add 0.5 parts of sodium dodecylsulfate under 30° C., and heat to 50° C. to react for 3 hours to let the particle surface coalescent with dodecyl group. Then rapidly heat up to 80° C. to remove ethyl acetate. Cool the system to room temperature until ethyl acetate is completely removed; add 150 parts of 35% thick hydrochloric acid to resolve the tricalcium phosphate on the surface of the toner particles.

Separate the liquid and the solid, disperse in ion exchange water the dehydrated toner press cake. Repeat this separation process for 3 times, wash and dry under 40° C. for 24 hours, to obtain toner particle Bk1.

Embodiments 2-29 for Preparing Polyester Expand Polymerized Toners and Comparative Embodiments 1-3 for Preparing Polyester Expand Polymerized Toners In the embodiment for preparing polyester expand polymerized toner 1, use the charge control agents listed in table 7 to replace the charge control agent (1-1), and other conditions are the same with that in the preparation of polyester expand polymerized toner 1, to obtain toner.

Hereafter, the polyester expand polymerized toners from using charge control agents (1-1) to charge control agent (2-10) listed in the table 7 are named toner (88)-toner (116). In addition, use chromium salicylate complex E-81 (manufactured by Orient Chemical Co), calixarene derivative E-88 (manufactured by Orient Chemical Co), and chromium azo complex S-34 (manufactured by Orient Chemical Co) as comparative charge control agents, to obtain comparative emulsion aggregated d toner, as shown in table 5, which are named comparative toner (10)-comparative toner (12).

Embodiments 1-116 and Comparative Embodiments 1-12

Mix the toners with carrier comprised of light metal ferrite coated with silicone and the volume average size of which is 65 μm, to obtain duel-component developers containing 8% toner.

Then name the duel-component developers using toner (1)-toner (116) as developer (1)-developer (116). And name the duel-component developers using comparative toner (1)-comparative toner (12) as comparative developer (1)-comparative developer (12).

Use the following method to evaluate the developer (1)-developer (116). The result is as shown in the following table 1-table 8.

Charge Characteristics

Weigh 1 g of the each kind of toners which are used to produce developer (1)-developer (116) and comparative developer (1)-comparative developer (12), separately put into a 20 ml glass test-tube with 10 g of carrier. Under 20° C. and 50% humidity RH environment, stir with YAYOI shaker for 1 minute, 2 minutes, 5 minutes, 10 minutes 20 minutes and 60 minutes. Under normal temperature and normal humidity, test with TB-200 charge amount testing apparatus (manufactured by Toshiba, Co.) to determine the charge amounts.

(2) Charge Stability

Weigh 1 g of the each kind of toners which are used to produce developer (1)-developer (116) and comparative developer (1)-comparative developer (12), separately put into a 20 ml glass test-tube with 10 g of carrier. Under normal temperature and normal humidity, test with TB-200 charge amount testing apparatus (manufactured by Toshiba, Co.) to determine the charge amounts (show in table 1 as initial charge amount). Then store in 35° C. and 85% humidity RH environment for 1 day and 1 night, test the charge amount again (show in table 1 as charge amount after storage).

(3) Imaging Quality

By contact imaging method and using respectively developer (1)-developer (116) and comparative developer (1) and comparative developer (12), in a photocopier (Ricoh Imagio Neo 1050Pro) which has a maximum speed of 105 ppm, under 20° C. and 50% humidity RH environment, as well as 35° C. and 85% humidity RH environment, to produce imaging of A4 size and pixel rate of 5%. The imaging copying mode is using A4 photocopy paper and pause for 1 minute after every 50 pages, for a total 500,000 pages. Test with 'RD-918' of Macbeth company the imaging density the black imaging of the initial imaging (show in table 2 and table 3 as 'initial') and the 500,000$^{th}$ imaging (show in table 2 and table 3 as '500,000$^{th}$'), and the fog density of blank space in these pages. The tests are conducted regarding the reflecting rate of the copying paper as '0', and to determine the relative reflect rate of the imaging.

In addition, observe the character resolution with a 10× magnifier on the initial imaging and the 500,000$^{th}$ imaging. While observe with eyes, test the toner charge amount after the initial imaging and after the 500,000$^{th}$ imaging.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

What is claimed is:

1. A toner containing at least a resin, a colorant and a charge control agent, the charge control agent comprising a specific type of gallic acid metal complex represented by the following Chemical Formula (1) or Chemical Formula (2):

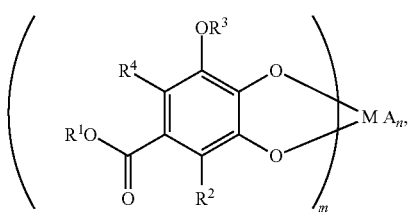

(1)

wherein in the formula (1), $R^1$ represents an alkyl group containing 1-12 carbon atoms, an alkenyl group containing 1-12 carbon atoms, a substituted or unsubstituted aryl group containing 6-12 carbon atoms, or a hydrogen atom; $R^2$ and $R^4$ can independently represent an alkyl group containing 1-12 carbon atoms, an alkenyl group containing 2-12 carbon atoms, an alkoxy group containing 1-12 carbon atoms, a substituted or unsubstituted aryl group containing 6-12 carbon atoms, a halogen atom, or a hydrogen atom; $R^3$ represents an alkyl group containing 1-12 carbon atoms, a substituted or unsubstituted aryl group containing 6-12 carbon atoms, a potassium atom, a sodium atom or a hydrogen atom; M represents a divalent to tetravalent metal atom, A is a counterion, m is a number from 1 to 3, and n is 1 or 2;

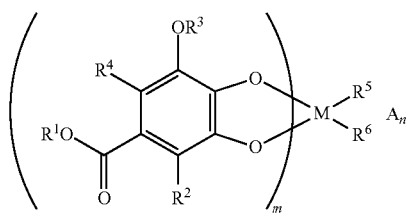

(2)

wherein in the formula (2), $R^1$ represents an alkyl group containing 1-12 carbon atoms, an alkenyl group containing 1-12 carbon atoms, a substituted or unsubstituted aryl group containing 6-12 carbon atoms, or a hydrogen atom; $R^2$ and $R^4$ independently represent an alkyl group containing 1-12 carbon atoms, an alkenyl group containing 2-12 carbon atoms, an alkoxy group containing 1-12 carbon atoms, a substituted or unsubstituted aryl group containing 6-12 carbon atoms, a halogen atom, or a hydrogen atom; $R^3$ represents an alkyl group containing 1-12 carbon atoms, a substituted or unsubstituted aryl group containing 6-12 carbon atoms, a potassium atom, a sodium atom or a hydrogen atom; $R^5$ and $R^6$ independently represent a carboxyl group, or a halogen atom; M represents a divalent to tetravalent metal atom, A is a counterion, m is a number from 1 to 3, and n is 1 or 2.

2. A toner comprising a resin, a colorant and a charge control agent, the charge control agent comprising a specific type of gallic acid metal complex represented by the following chemical formula

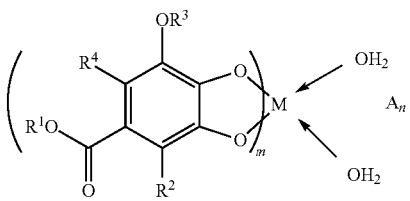

wherein $R^1$ represents an alkyl group containing 1-12 carbon atoms, an alkenyl group containing 1-12 carbon atoms, a substituted or unsubstituted aryl group containing 6-12 carbon atoms, or a hydrogen atom; $R^2$ and $R^4$ independently represent an alkyl group containing 1-12 carbon atoms, an alkenyl group containing 2-12 carbon atoms, an alkoxy group containing 1-12 carbon atoms, a substituted or unsubstituted aryl group containing 6-12 carbon atoms, a halogen atom, or a hydrogen atom; $R^3$ represents an alkyl group containing 1-12 carbon atoms, a substituted or unsubstituted aryl group containing 6-12 carbon atoms, a potassium atom, a sodium atom or a hydrogen atom; M represents a divalent to tetravalent metal atom, A is a counterion, m is a number from 1 to 3, and n is 1 or 2.

* * * * *